US008672884B2

(12) United States Patent
Burnett et al.

(10) Patent No.: US 8,672,884 B2
(45) Date of Patent: Mar. 18, 2014

(54) METHOD AND APPARATUS FOR PERITONEAL HYPOTHERMIA AND/OR RESUSCITATION

(75) Inventors: Daniel R Burnett, San Francisco, CA (US); Shane Mangrum, Idaho Falls, ID (US); Jared C Blanton, Mill Valley, CA (US)

(73) Assignee: Velomedix, Inc., Menlo Park, CA (US)

( * ) Notice: Subject to any disclaimer, the term of this patent is extended or adjusted under 35 U.S.C. 154(b) by 2320 days.

(21) Appl. No.: 11/552,090

(22) Filed: Oct. 23, 2006

(65) Prior Publication Data

US 2007/0106247 A1    May 10, 2007

Related U.S. Application Data

(60) Provisional application No. 60/728,785, filed on Oct. 21, 2005.

(51) Int. Cl.
*A61F 7/12* (2006.01)
*A61M 31/00* (2006.01)

(52) U.S. Cl.
USPC .......................................... 604/113; 604/506

(58) Field of Classification Search
USPC .............. 604/113–114, 26, 29, 508, 140–147
See application file for complete search history.

(56) References Cited

U.S. PATENT DOCUMENTS

| 2,078,786 A | 4/1937 | Wood |
| 3,042,042 A | 7/1962 | Blanck |
| 3,505,988 A | 4/1970 | Deane |
| 3,698,396 A | 10/1972 | Katerndahl et al. |
| 3,927,980 A | 12/1975 | Leonard |
| 4,356,826 A | 11/1982 | Kubota |
| 4,413,633 A | 11/1983 | Yanda |
| 4,445,500 A | 5/1984 | Osterholm |

(Continued)

FOREIGN PATENT DOCUMENTS

| GB | 2267829 A | 12/1993 |
| WO | WO 93/13718 A1 | 7/1993 |

(Continued)

OTHER PUBLICATIONS

Burnett et al.; U.S. Appl. No. 12/169,566 entitled "Hypothermia devices and methods," filed Jul. 8, 2008.

(Continued)

*Primary Examiner* — Jason Flick
*Assistant Examiner* — Weng Lee
(74) *Attorney, Agent, or Firm* — Shay Glenn LLP

(57) ABSTRACT

Embodiments of the invention provide apparatus, systems and methods for introducing fluids into a body cavity for hypothermic, resuscitative, or other treatment. One embodiment provides an apparatus for introducing fluids into a peritoneal cavity comprising an access device for insertion into subcutaneous tissue, an infusion member and an advancement member. The access device includes a lumen, a proximal end, a tissue penetrating distal end and a stop for controlling the depth of the distal end into tissue. The infusion member includes an infusion lumen, a removal lumen and at least one sensor and is advanceable from a lumen of the access device into the peritoneal cavity. The advancement member is removably positionable in an infusion member lumen and has sufficient column strength to advance the infusion member tip through abdominal wall tissue into the peritoneal cavity. When the advancement member is removed, the infusion member tip is substantially atraumatic.

48 Claims, 18 Drawing Sheets

(56) References Cited

U.S. PATENT DOCUMENTS

| | | | |
|---|---|---|---|
| 4,450,841 A | 5/1984 | Osterholm | |
| 4,497,324 A | 2/1985 | Sullivan et al. | |
| 4,535,773 A | 8/1985 | Yoon | |
| 4,813,429 A | 3/1989 | Eshel et al. | |
| 4,883,459 A | 11/1989 | Calderon | |
| 4,904,237 A | 2/1990 | Janese | |
| 4,963,130 A | 10/1990 | Osterholm | |
| 5,112,267 A | 5/1992 | Liu et al. | |
| 5,141,493 A | 8/1992 | Jacobsen et al. | |
| 5,149,321 A | 9/1992 | Klatz et al. | |
| 5,245,367 A | 9/1993 | Miller et al. | |
| 5,249,585 A | 10/1993 | Turner et al. | |
| 5,344,136 A | 9/1994 | Capdeboscq | |
| 5,354,277 A | 10/1994 | Guzman et al. | |
| 5,380,160 A | 1/1995 | Chen | |
| 5,478,329 A | 12/1995 | Ternamian | |
| 5,554,280 A | 9/1996 | Loehr | |
| 5,562,821 A | 10/1996 | Gutierrez-Collazo | |
| 5,665,227 A | 9/1997 | Watt | |
| 5,693,017 A * | 12/1997 | Spears et al. | 604/132 |
| 5,709,654 A | 1/1998 | Klatz et al. | |
| 5,709,661 A | 1/1998 | Van Egmond et al. | |
| 5,730,720 A | 3/1998 | Sites et al. | |
| 5,752,929 A | 5/1998 | Klatz et al. | |
| 5,755,756 A | 5/1998 | Freedman, Jr. et al. | |
| 5,916,153 A | 6/1999 | Rhea, Jr. | |
| 6,019,729 A | 2/2000 | Itoigawa et al. | |
| 6,019,783 A | 2/2000 | Philips et al. | |
| 6,066,163 A | 5/2000 | John | |
| 6,117,076 A | 9/2000 | Cassidy | |
| 6,126,684 A | 10/2000 | Gobin et al. | |
| 6,146,411 A | 11/2000 | Noda et al. | |
| 6,149,624 A | 11/2000 | McShane | |
| 6,149,670 A | 11/2000 | Worthen et al. | |
| 6,165,207 A | 12/2000 | Balding et al. | |
| 6,175,688 B1 | 1/2001 | Cassidy et al. | |
| 6,188,930 B1 | 2/2001 | Carson | |
| 6,197,045 B1 | 3/2001 | Carson | |
| 6,254,567 B1 | 7/2001 | Treu et al. | |
| 6,264,680 B1 | 7/2001 | Ash | |
| 6,287,326 B1 | 9/2001 | Pecor | |
| 6,290,717 B1 | 9/2001 | Philips | |
| 6,299,599 B1 | 10/2001 | Pham et al. | |
| 6,304,776 B1 | 10/2001 | Muntermann | |
| 6,338,727 B1 | 1/2002 | Noda et al. | |
| 6,368,304 B1 | 4/2002 | Aliberto et al. | |
| 6,375,674 B1 | 4/2002 | Carson | |
| 6,379,331 B2 | 4/2002 | Barbut et al. | |
| 6,405,080 B1 | 6/2002 | Lasersohn et al. | |
| 6,409,699 B1 | 6/2002 | Ash | |
| 6,419,643 B1 | 7/2002 | Shimada et al. | |
| 6,436,295 B2 | 8/2002 | Kim | |
| 6,447,474 B1 | 9/2002 | Balding | |
| 6,450,990 B1 | 9/2002 | Walker et al. | |
| 6,451,045 B1 | 9/2002 | Walker et al. | |
| 6,458,150 B1 | 10/2002 | Evans et al. | |
| 6,460,544 B1 | 10/2002 | Worthen | |
| 6,461,379 B1 | 10/2002 | Carson et al. | |
| 6,480,257 B2 | 11/2002 | Cassidy et al. | |
| 6,497,721 B2 | 12/2002 | Ginsburg et al. | |
| 6,520,933 B1 | 2/2003 | Evans et al. | |
| 6,529,775 B2 | 3/2003 | Whitebook et al. | |
| 6,530,945 B1 | 3/2003 | Noda et al. | |
| 6,530,946 B1 | 3/2003 | Noda et al. | |
| 6,537,241 B1 | 3/2003 | Odland | |
| 6,551,302 B1 | 4/2003 | Rosinko et al. | |
| 6,554,797 B1 | 4/2003 | Worthen | |
| 6,572,640 B1 | 6/2003 | Balding et al. | |
| 6,579,496 B1 | 6/2003 | Fausset et al. | |
| 6,581,403 B2 | 6/2003 | Whitebook et al. | |
| 6,582,398 B1 | 6/2003 | Worthen et al. | |
| 6,585,692 B1 | 7/2003 | Worthen | |
| 6,602,243 B2 | 8/2003 | Noda | |
| 6,620,187 B2 | 9/2003 | Carson et al. | |
| 6,641,602 B2 | 11/2003 | Balding | |
| 6,641,603 B2 | 11/2003 | Walker et al. | |
| 6,645,232 B2 | 11/2003 | Carson | |
| 6,645,234 B2 | 11/2003 | Evans et al. | |
| 6,648,905 B2 | 11/2003 | Hoglund et al. | |
| 6,660,027 B2 | 12/2003 | Gruszecki et al. | |
| 6,669,715 B2 | 12/2003 | Hoglund et al. | |
| 6,676,409 B2 | 1/2004 | Grant | |
| 6,682,551 B1 | 1/2004 | Worthen et al. | |
| 6,685,733 B1 | 2/2004 | Dae et al. | |
| 6,692,518 B2 | 2/2004 | Carson | |
| 6,699,267 B2 | 3/2004 | Voorhees et al. | |
| 6,699,268 B2 | 3/2004 | Kordis et al. | |
| 6,704,590 B2 | 3/2004 | Haldeman | |
| 6,706,060 B2 | 3/2004 | Tzeng et al. | |
| 6,709,448 B2 | 3/2004 | Walker et al. | |
| 6,716,236 B1 | 4/2004 | Tzeng et al. | |
| 6,719,724 B1 | 4/2004 | Walker et al. | |
| 6,733,517 B1 | 5/2004 | Collins | |
| 6,743,218 B2 | 6/2004 | Maginot et al. | |
| 6,749,625 B2 | 6/2004 | Pompa et al. | |
| 6,764,391 B1 | 7/2004 | Grant et al. | |
| 6,796,995 B2 | 9/2004 | Pham et al. | |
| 6,799,063 B2 | 9/2004 | Carson | |
| 6,802,855 B2 | 10/2004 | Ellingboe et al. | |
| 6,807,444 B2 | 10/2004 | Tu et al. | |
| 6,818,012 B2 | 11/2004 | Ellingboe | |
| 6,819,950 B2 | 11/2004 | Mills | |
| 6,827,728 B2 | 12/2004 | Ellingboe et al. | |
| 6,827,898 B1 | 12/2004 | Fausset et al. | |
| 6,878,156 B1 | 4/2005 | Noda | |
| 6,893,454 B2 | 5/2005 | Collins | |
| 6,921,198 B2 | 7/2005 | Gruszecki et al. | |
| 6,981,945 B1 | 1/2006 | Sarvazyal et al. | |
| 7,001,418 B2 | 2/2006 | Noda | |
| 7,008,444 B2 | 3/2006 | Dae et al. | |
| 7,070,612 B1 | 7/2006 | Collins et al. | |
| 7,090,792 B1 | 8/2006 | Balding et al. | |
| 7,097,657 B2 | 8/2006 | Noda et al. | |
| 7,144,407 B1 | 12/2006 | Lasersohn | |
| 7,181,927 B2 | 2/2007 | Collins et al. | |
| 7,255,709 B2 | 8/2007 | Walker et al. | |
| 7,278,984 B2 | 10/2007 | Noda et al. | |
| 7,287,398 B2 | 10/2007 | Noda et al. | |
| 7,361,186 B2 | 4/2008 | Voorhees et al. | |
| 7,425,216 B2 | 9/2008 | Collins | |
| 7,566,341 B2 | 7/2009 | Keller et al. | |
| 2002/0026094 A1 | 2/2002 | Roth | |
| 2002/0033181 A1 | 3/2002 | Groth et al. | |
| 2003/0131844 A1 | 7/2003 | Kumar et al. | |
| 2004/0087606 A1 | 5/2004 | Voorhees et al. | |
| 2004/0102826 A1 | 5/2004 | Lasheras et al. | |
| 2004/0122353 A1 | 6/2004 | Shahmirian et al. | |
| 2004/0138701 A1 * | 7/2004 | Haluck | 606/205 |
| 2004/0158119 A1 | 8/2004 | Osorio et al. | |
| 2004/0193098 A1 | 9/2004 | Wentling et al. | |
| 2004/0231664 A1 | 11/2004 | Lurie et al. | |
| 2005/0033391 A1 | 2/2005 | Worthen et al. | |
| 2005/0177212 A1 | 8/2005 | Njemanze | |
| 2005/0203598 A1 | 9/2005 | Becker et al. | |
| 2006/0064146 A1 | 3/2006 | Collins | |
| 2006/0161107 A1 | 7/2006 | Mantle | |
| 2006/0190066 A1 | 8/2006 | Worthen | |
| 2006/0276864 A1 | 12/2006 | Collins | |
| 2006/0293734 A1 | 12/2006 | Scott et al. | |
| 2007/0045188 A1 | 3/2007 | Blanton | |
| 2007/0051409 A1 | 3/2007 | Landy, III et al. | |
| 2007/0203552 A1 | 8/2007 | Machold et al. | |
| 2008/0045867 A1 | 2/2008 | Jensen et al. | |
| 2008/0249467 A1 | 10/2008 | Burnett et al. | |
| 2008/0262418 A1 | 10/2008 | Burnett et al. | |

FOREIGN PATENT DOCUMENTS

| | | |
|---|---|---|
| WO | WO 98/04191 A1 | 2/1998 |
| WO | WO 00/48670 A1 | 8/2000 |
| WO | WO 00/72779 A2 | 12/2000 |
| WO | WO 01/03606 A2 | 1/2001 |
| WO | WO 01/17471 A1 | 3/2001 |
| WO | WO 01/39819 A2 | 6/2001 |

(56) References Cited

FOREIGN PATENT DOCUMENTS

| WO | WO 01/41708 A2 | 6/2001 |
|----|----------------|--------|
| WO | WO 01/58509 A1 | 8/2001 |
| WO | WO 02/26175 A1 | 4/2002 |
| WO | WO 02/26176 A1 | 4/2002 |
| WO | WO 02/26285 A2 | 4/2002 |
| WO | WO 02/26307 A1 | 4/2002 |
| WO | WO 02/058606 A1 | 8/2002 |
| WO | WO 03/059218 A1 | 7/2003 |
| WO | WO 2006/060514 A1 | 6/2006 |

OTHER PUBLICATIONS

Davison et al.; Epidural cooling for regional spinal cord hypothermia during thoracoabdominal aneurysm repair; J. Vasc. Surg.; vol. 20(2); No. 304-10; Aug. 1994 (Abstract Only).

Burnett et al.; U.S. Appl. No. 12/615,045 entitled "Devices and Methods for Monitoring Core Temperature and an Intraperitoneal Parameter," filed Nov. 9, 2009.

Hall et al.; U.S. Appl. No. 12/702,165 entitled "Method and Apparatus for Inducing Therapeutic Hypothermia," filed Feb. 8, 2010.

Polderman et al.; Effects of therapeutic hypothermia on intracranial pressure and outcome in patients with severe head injury; Intensive Care Med; vol. 28; pp. 1563-1573; 2002.

Demling et al.; Initial management of burn patient; (from Burnsurgery.org); 2004.

Rutherford et al.; Management of the patient with an open abdomen: techniques in temporary and definitive closure; Curr Probl Surg; vol. 41; pp. 821-876; 2004.

Sieh et al.; Intra-abdominal hypertension and abdominal compartment syndrome; Langenbeck's Arch Surg; vol. 386; pp. 53-61; 2001.

Hwang et al.; Peri-operative concerns in thoracic trauma; Bailliére's Clinical Anaesthesiology; vol. 10; No. 1; pp. 123-153; 1996.

Stover et al.; Treating intracranial hypertension in patients with severe traumatic brain injury during neurointensive care; European Journal of Trauma; 2005(4); pp. 308-330; 2005.

Sedlak, S. Kay; Hypothermia in trauma: the nurse's role in recognition, prevention, and management; Int'l Journal of Trauma Nursing; ; vol. 1; No. 1; pp. 19-26; Jan. 1995.

\* cited by examiner

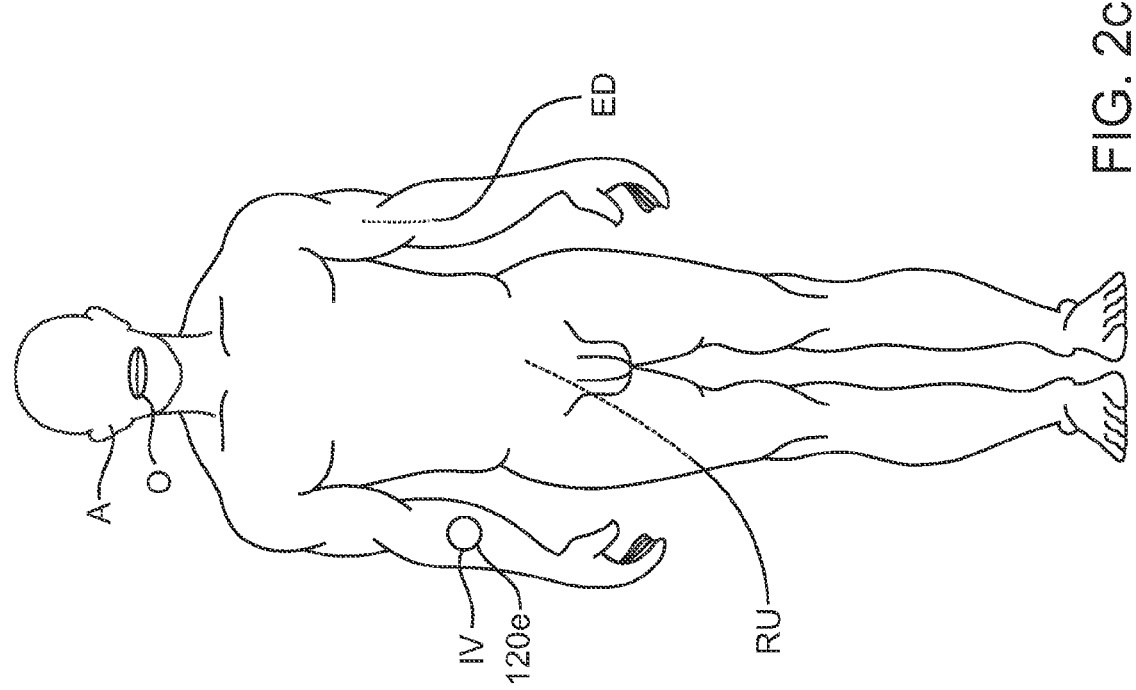

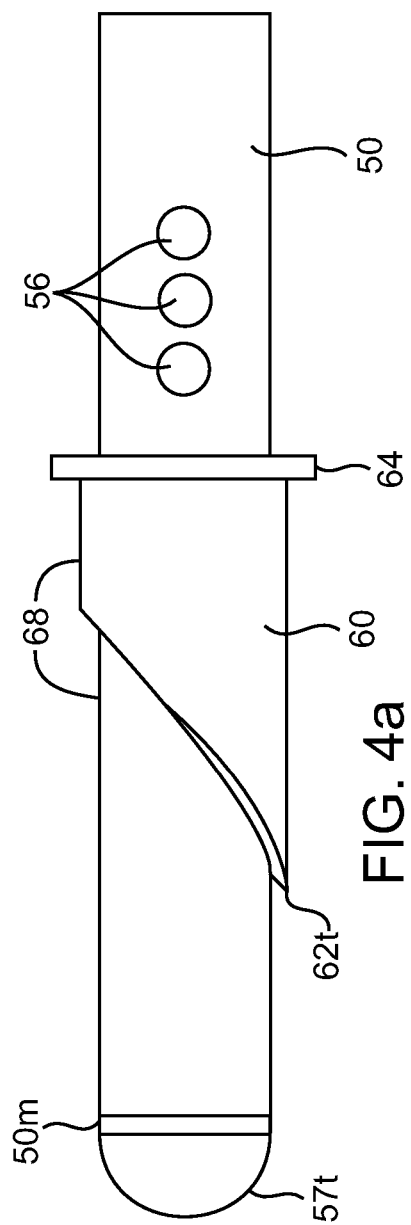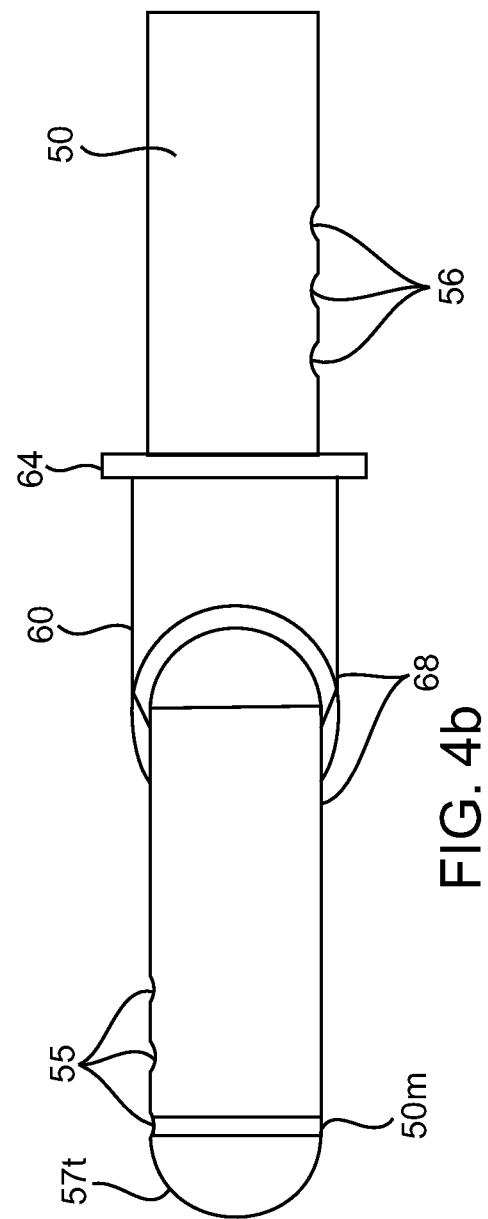

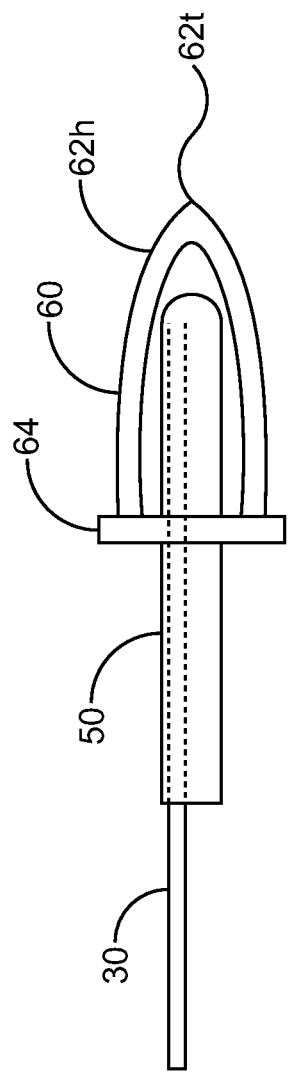
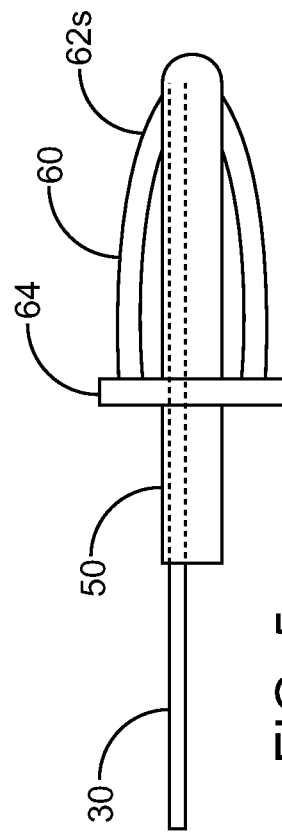
FIG. 5f
FIG. 5g

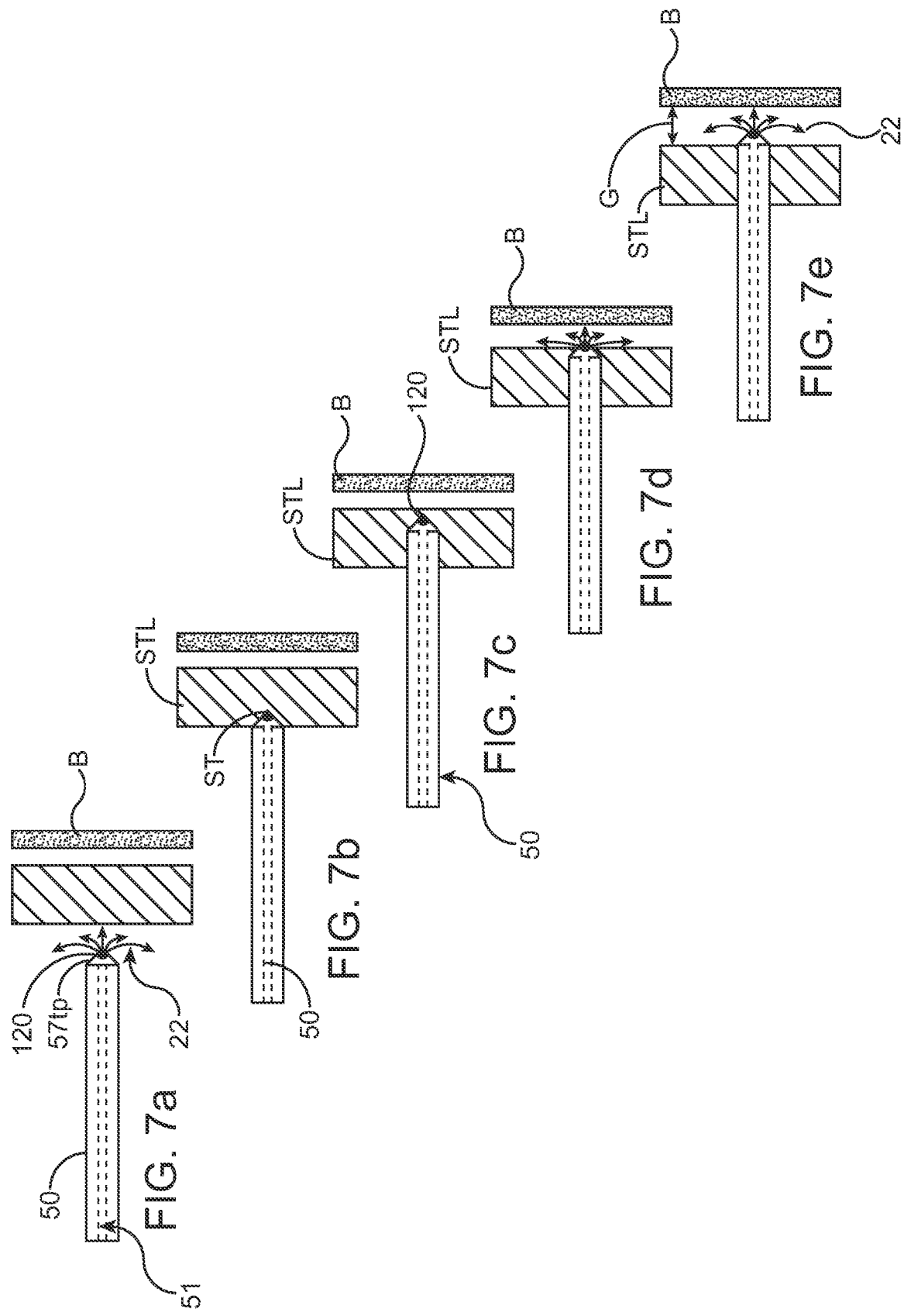

METHOD AND APPARATUS FOR PERITONEAL HYPOTHERMIA AND/OR RESUSCITATION

CROSS-REFERENCES TO RELATED APPLICATIONS

This application claims the benefit of priority U.S. Provisional Patent Application Ser. No. 60/728,785 filed on Oct. 21, 2005, the full disclosure of which is incorporated herein by reference.

BACKGROUND OF THE INVENTION

Field of the Invention

Embodiments of the invention relate to apparatus and methods for providing therapeutic hypothermia treatment to a patient. More specifically embodiments of the invention relate to apparatus and methods for providing therapeutic hypothermia to a patient as well as resuscitation using extracorporeal peritoneal circulation.

Hypothermia has been shown to provide distinct medical benefits to stroke and cardiac arrest patients by limiting the size of the infarction and related tissue injury if initiated soon enough and if the level of cooling is significant enough. Both of these limitations, initiation of and depth of cooling, have made practical application of the technology quite challenging particularly in an ambulance or other emergency settings in the field. Initiation of cooling, for example, is a major issue since most technologies require sophisticated machinery that would be difficult to place in ambulance so the patient, at best, receives the hypothermic benefit some time after they reach the hospital. Of the technologies that can be initiated in the field, though, such as cooling blankets, cooling caps, etc., the depth of cooling is a major issue due to surface area limitations, complications (such as intense shivering response) and patient access issues (once the blanket is on, it may be difficult to access the patient).

Thus, there exists a need for improved devices for rapidly producing hypothermia to treat stroke, severe cardiac events and related conditions, particularly in field settings.

BRIEF SUMMARY OF THE INVENTION

Embodiments of the invention provide apparatus, systems and methods for achieving therapeutic hypothermia using minimally invasive access of the peritoneal cavity or other body cavity. Such embodiments can use minimally invasive methods to deliver and circulate hypothermic solutions to the peritoneal or other body cavity to reduce body temperature to a selected level for treatment of a number of medical conditions where there is diminished perfusion to one or more locations in the body. Such conditions can include various cardiac conditions including myocardial infarction and cardiac arrest; cerebral conditions including stroke and head trauma; and various hemorrhagic events due to arterial dissection or rupture or trauma. Particular hypothermic regimens (e.g., temperature and rate of cooling) can be employed to treat particular conditions e.g. stroke vs. myocardial infarction so as to reduce the amount of ischemic reperfusion injury to vital organs resulting from the particular ischemic event. Also, embodiments can have hypothermic regimens for various surgical procedures to reduce the amount of post-surgical inflammation and to provide a tissue protective effect so as to extend the operating times for various procedures which require reduced perfusion at the surgical site or throughout the body. Examples of the latter application can include open-heart procedures where the heart can be cooled to allow for longer periods where the heart is arrested and neurosurgical procedures to provide a neuro-protective effect for tissue at or near the operative site. Selection of a particular hypothermic regimen can be made by the user from a database of regimens stored in memory resources within a system control unit (e.g., a console) or otherwise electronically coupled to the system either directly or wirelessly. In particular embodiments, the hypothermic regimen can be stored in a flash memory or other non-volatile memory device coupled to a disposable catheter set or kit used by the system. The memory device could then interface and upload the regimen to the control device, for example a docking station that the flash memory device plugs in to. RF and other wireless interfaces to the system control device using BLUE TOOTH or another protocol are also contemplated.

These and related embodiments can also be utilized for patient resuscitation from various ischemic, hemorrhagic events (e.g., stroke, or cardiac arrest) as well as shock through the use of peritoneal therapeutic solutions which can be used to oxygenate ischemic tissue, reduce reperfusion injury, and increase blood pressure by exerting a compressive force against the peritoneal or other body cavity vasculature. Such therapeutic solutions can include various peritoneal dialysis solutions which can comprise nutrients and one or more reperfusion injury protective agents. Also, the solution can comprise oxygenated solutions such as oxygenated flourocarbon solutions that can be configured to deliver sufficient oxygen to tissue (by gas exchange with peritoneal or other surrounding tissue) to at least partially meet the oxygen demands of the body. For embodiments of the invention used to treat shock, the solution need not be chilled and can actually be warmed.

Also, many embodiments of the invention can be configured as a portable body cavity infusion/hypothermic system that can be readily transported in an ambulance, carried and used at a trauma scene by EMT's, military medics and emergency room personnel. Thus, one or more components of the system can include a handle, or the entire system can be integrated into an assembly having a handle. Further, as described herein, embodiments of a portable system can be configured for ease of use so as to require minimal set up time and manual dexterity by medical personnel. For example, embodiments of the system can use a sub-cutaneous access device that uses a stop or other means to control the depth of penetration into subcutaneous tissue so that the user need not have to precisely position the access device. This access device can be used in conjunction with an infusion catheter having a sensor configured to alert the user when the catheter has entered the peritoneal cavity so as to minimize or eliminate the risk of injuring a peritoneal organ. The infusion catheter can make use of quick connections for rapid connection to liquid and gas sources, fluid collection devices and other system components. The subsequent infusion and thermal control of fluids can then be automated through use of a computer controller or other electronic controller. In use, such embodiments provide a system with a fast set up time, high degree of reproducibility, and requires minimal dexterity and training of medical personnel.

One embodiment of the invention provides an apparatus for accessing and introducing fluids into the peritoneal or other cavity of a patient to produce hypothermia. The apparatus comprise an access device configured to be inserted into subcutaneous tissue, an infusion member and an advancement member. The access device includes a lumen, a proximal end, a tissue penetrating distal end and a stop. The access device can include a surgical port device. The stop is configured to control the penetration depth of the distal end of the access device into tissue, such as the subcutaneous tissue of the abdominal wall or other tissue wall. The stop can also include an adhesive or suture opening to affix or otherwise immobilize the access device on the surface of the skin. The stop can also be adjustable (e.g. by indexing) to allow the user to select the penetration depth. By controlling the penetration depth of the access device, the stop serves to make the insertion procedure more reproducible, less technique dependant, and reduces the risk of over insertion.

In various embodiments, the distal end of the access device can also be transformable from a tissue penetrating configuration to a non-tissue penetrating safety configuration. This can be achieved by configuring the distal end to be retractable, to be shearable (e.g., by the advancement member) or to have an overlying movable sheath which is withdrawn during advancement and covers the distal end once the access device is positioned. In use, the transformable distal end serves to further improve the safety of the insertion procedure by reducing the risk of inadvertent tissue injury once the access device is positioned.

The infusion member can be positioned within a lumen of the access device and be advanceable into the peritoneal or other body cavity. The infusion member can include a tissue penetrating distal end to allow advancement from subcutaneous tissue into the peritoneal cavity. The tip can be constructed from flexible materials such that when it is not supported by the advancement member it is substantially atraumatic. The tip or other portion of the infusion member can also include one or more sensors configured to sense one or more of flow through the infusion member, pressure or temperature. In particular embodiments, the sensor can be a flow or pressure sensor configured to determine when the tip has entered the peritoneal or other cavity so as to minimize the chances of injuring a peritoneal organ during infusion member advancement.

Typically, the infusion member will include a first lumen and a second lumen for the infusion and removal of fluid into and out of the peritoneal or other cavity. Additional lumens are also contemplated, for example for a guide wire, introduction of medicaments or as dedicated sensing lumens. The lumen can be can extend over all or a portion of the length of the infusion member. The first lumen or infusion lumen allows for the infusion of hypothermic solutions (also called infusate) into the peritoneal cavity so as to produce selected amounts of hypothermia from heat exchange with the hypothermic solution, the peritoneal organs and tissue. In various embodiments, the infusion lumen can be sized to allow the delivery of sufficient hypothermic solutions into the peritoneal cavity to produce a drop in body temperature of 3° C. or more within ten minutes or less. Lumen sizes to produce temperature reductions of 5 or even 10° C. are also contemplated. The second lumen or removal lumen can be sized to allow for the removal of solution at a rate equal to that infused. The removal lumen is desirably not continuous to the very tip of the infusion member to allow for the advancement member to have a surface to push against so as to advance the infusion member. Alternatively, the removal lumen can neck down near the distal end of the infusion lumen so as to be able to hold the advancement member by an interference fit.

Typically, the infusion member will include one or more apertures coupled to the first and second lumen. Those coupled to the first lumen can be positioned at the distal end of the infusion member for the outflow of the infusate solution. The aperture(s) can be positioned so as to reduce the likelihood of obstruction by tissue when the infusion member is advanced, for example by positioning the aperture on a side of the tip or placing the aperture behind a barrier coupled to the infusion member. The apertures coupled to the second lumen can comprise a plurality of apertures distributed along a length of the distal portion of the infusion member. The spacing of the apertures can be configured to maintain patency of at least a portion of the apertures when inserted in the peritoneal cavity, and still maintain the flexibility and structural integrity of the infusion member.

In particular embodiments, the infusion member can comprise a flexible catheter fabricated from flexible biocompatible polymers known in the art, such as silicone or polyurethane. In a preferred embodiment, the infusion member comprises a dual lumen flexible infusion catheter, with one lumen for infusion of various solutions and a second for removal. Also, the distal tip or other portion of the infusion catheter can be tapered to provide additional flexibility. The proximal end of the catheter can include a luer lock or other fitting or adapter (e.g., a Y adapter) for quick connection to one or more fluid, gas, pressure and vacuum sources, and fluid receptacles. The proximal end or other portions of the catheter can also include a flash memory device (with an embedded infusion control/hypothermic regimen software module) that plugs into a system control device described herein. Also, the infusion catheter can be configured to be kink resistant for example through the use of braiding (internal or external) or other supporting means. Braiding can also be configured to provide for use of higher infusion pressures, for example during rapid infusion of a bolus of hypothermic solution.

The advancement member is removably positionable in at least one of the two lumens, and desirably has sufficient column strength to advance the infusion member through the abdominal wall or other tissue and into the peritoneal cavity by manipulation of a proximal portion of the infusion member or the advancement member. Ideally, the advancement member has a length such that the proximal end of the advancement member extends past the proximal portion of the infusion member (when fully inserted into the infusion member) so that the proximal end of the advancement member can be readily manipulated by the user. Desirably, the advancement member will have a handle or grip at it's proximal portion. The diameter of the advancement member is sized such that it can be readily advanced or withdrawn from the infusion member with minimal, or in some cases, slight resistance. In various embodiments, the advancement member can be fabricated from various metals such as stainless steal or rigid polymers known in the art. In addition to having sufficient column strength to advance the infusion member, the advancement member can also be configured to have sufficient column strength to push (i.e., shear) through the inner distal end of embodiments of the access device that have a shearable distal end.

Typically, the advancement member will be positioned in the removal lumen so as to allow for flow of solution through the infusion lumen during advancement of the infusion catheter. Also, the infusion member can have a touhy-borst type of adjustable valve positioned around the advancement member to form a fluidic seal around the advancement member during movement or when stationary. The valve can also be configured to fluidicaly seal the proximal end of the removal lumen when the advancement member is not in place. The adjustable valve can be configured to not only form a fluidic seal around the advancement member, but also to hold the advancement member in place within the infusion catheter. This allows the user to selectively position the advancement member in the infusion catheter during advancement of the latter. This positioning, in turn, can allow the user to select the amount of flexibility or stiffness of the distal portions of the infusion catheter.

An exemplary embodiment of a method for using one or more of the above embodiments to deliver fluid to a body cavity of a patient for hypothermic or other treatments can comprise inserting the access port or other access device a controlled depth into a tissue wall of the patient. The access port can then be fixed in place via an adhesive or through use of a suture put through tissue and a suture eyelet or other opening on the access port. An infusion catheter or other infusion member can then be through the access port utilizing through use of a rigid advancement member positioned in the infusion catheter. The point when the distal tip of the infusion member enters the body cavity can then be determined using one or more sensors configured to sense properties such as force, pressure or fluid flow rate through the infusion member. In the latter two cases, the infusion member can be connected to the fluid pressure source during advancement with entry determined by an increase in flow rate or a decrease in pressure. Once entry is sensed, a control unit coupled to the sensor can output an audio alarm or other signal to medical personnel to alert them of the entry so they can stop advancing the infusion member to prevent penetration injury of organs within the cavity. The advancement member is then removed from the infusion member so as to render the distal tip of the infusion member substantially atraumatic. Various hypothermic, nutrient and other solutions can then be infused into the cavity through the infusion member to achieve a desired hypothermic, resuscitative or other medical effects or a combination thereof. In various embodiments, this method can be used to infuse fluid into a peritoneal cavity to achieve a desired level of hypothermia for treating one or more of cardiac arrest, myocardial infarction, stroke, head or other trauma, hemorrhage or post-surgical inflammation. Similar effects can be achieved by infusing such fluids into the pleural or other body cavity.

Another embodiment provides an apparatus for accessing and introducing fluids into a peritoneal cavity of a patient in order to achieve selected levels of hypothermia. The apparatus comprises an access device configured to be inserted through the abdominal wall and into the peritoneal cavity, an infusion member positionable within a lumen of the access device and advanceable into the peritoneal cavity. The access device includes a lumen, a proximal and a distal end having a tissue penetrating configuration and a non-tissue penetrating safety configuration. The access device is transformable to the safety configuration upon penetration through an abdominal wall. The infusion member includes at least one lumen for the infusion or removal of fluid into or out of the peritoneal cavity. The lumen is sized to deliver sufficient fluid to the cavity to reduce the patient's body temperature by at least about 3° C. through heat exchange with peritoneal tissue.

Another embodiment provides a system for producing hypothermia in a patient comprising the above apparatus; a fluid reservoir operatively coupled to infusion member; a pressure source operatively coupled to the reservoir; a vacuum source operatively coupled to infusion member; at least one sensor operatively coupled to at least one of the pressure source, the vacuum source or the infusion member; a control unit operatively coupled to at least one of the pressure source, the vacuum source, the infusion member or the at least one sensor. At least one valve can also be operatively coupled to the control unit and one of the infusion member or the pressure source. The valve can be a control valve and can be configured to control fluid flow to or from the peritoneal cavity, responsive to a signal from the control unit. A cooling device such as a peltier cooling device can be operatively coupled to the fluid reservoir or the infusion member. The cooling device is configured to cool fluid within, for flowing from the fluid reservoir.

The pressure source is configured to deliver fluid from the reservoir through the infusion member and into the peritoneal cavity. The pressure source can comprise a compressed gas source, an oxygen pressure source, a compressed oxygen source, a pump or a gravity generated pressure source (e.g., an I.V bag on a pole). The vacuum source is configured to provide sufficient vacuum pressure for removing fluid from the peritoneal cavity and can be generated by a vacuum pump or can be an external source. The sensor can comprise a pressure, temperature or flow sensor. The control unit can be configured for controlling one or more aspects of the process used to produce hypothermia such as the infusion and removal of the hypothermic solution, temperature control and oxygenation of the solution, the infusion pressure and the vacuum pressure and the total amount of solution infused and removed from the peritoneal cavity. The control unit can include logic resources such as a processor, as well as memory resources. The control unit can also be configured to interface with logic and memory resources (such as flash memory) coupled to the infusion member or other system component.

An exemplary embodiment of a method of using the above system can comprise inserting the access port or other access device a controlled depth into an abdominal wall of the patient. The access port can then be fixed in place as described above. An infusion catheter or other infusion member can then be advanced through the access port using an advancement member until the user receives an audible alarm or other signal indicating the tip of the infusion catheter has entered the peritoneal cavity, as described above, so that advancement is stopped before contact with the peritoneal organs is made, reducing or eliminating the risk or peritoneal organ injury (Peritoneal injury can also be mitigated blowing air through the infusion catheter during advancement to push away any peritoneal organ tissue). The advancement member can then be removed to render the tip of the infusion catheter atraumatic. The user can then continue to advance the infusion catheter a desired amount in the cavity (e.g., to position catheter, apertures or sensors in the cavity) without the risk of tissue injury. This can be facilitated by the placement of depth markings on the catheter shaft.

The temperature of the patient can then be monitored using temperature sensors positioned on the infusion catheter, as well as other locations in the body such as the tympanic membrane, or an intravenous site. Various hypothermic, nutrient and other solutions can then be infused into the cavity through the infusion member wherein an infusion parameter, such as flow rate or total infused volume, is controlled using the monitored temperature. The hypothermic solution then cools the peritoneal organs and other peritoneal tissue so as to reduce the patient's temperature to a selected level. In various embodiments, the patient's body temperature can be reduced in the amount of 3, 5, 10° C. or greater. In preferred embodiments, the patient's temperature can be reduced to a range between about 32 to 34° C. Temperature reduction can be done in ten minutes or less depending on the desired level of cooling and the particular condition to be treated. Faster rates of cooling can be selected depending upon the severity of the patient's condition and/or how soon the patient is first treated after a particular medical event (e.g., heart attack). Also, a database of cooling rates can be developed and used which takes into account the particular medical condition, vital statistics of the patient (e.g. weight and age) and the estimated time post event (e.g., time from the onset of stroke). The database can be developed for both populations (e.g., all heart attack patients) and sub-populations of patients (e.g., those over 65).

Infusion can be performed in a variety of modes. It can be done rapidly using a bolus of hypothermic solution, or it can be done more gradually, or a combination of rapid and slower infusion modes can be used. In preferred embodiments, a bolus of solution is infused so as to expand the peritoneal cavity and the space between peritoneal organs so as to increase the peritoneal tissue surface area available for heat and mass transfer with the hypothermic or other solution. In various embodiments, the bolus can comprise between about 0.5 to three liters of hypothermic solution in the temperature range from −10 to 20° C. In a preferred embodiment, about two liters of 4° C. solution is delivered in about ten minutes or less.

The delivery of the bolus can be followed by a mode where fluid is infused at a slower rate and then removed with infusion and removal rates based on temperatures measured in the peritoneal cavity and elsewhere in the body. The two modes of delivery can also overlap. Rates can be controlled through the use of an automated valve and/or automated pump. Desirably, the infusion and removal rates are also controlled to keep a sufficient proportion of the bolus volume in the peritoneal cavity to maintain the cavity in the expanded state for enhanced heat and mass transfer with the infused solution. The infusion and removal rates can also be controlled to assure that there is not overfilling or excessive pressure buildup within the peritoneal or other cavity. This can be facilitated by monitoring pressures within the peritoneal cavity and/or the pressures within the infusion catheter. In other embodiments, expansion of the peritoneal cavity can also be achieved through the use of compressed air (e.g., using compressed gas source 92) in an insufflation technique known in the art to create a pneumoperitoneum.

Infusion and removal can be performed concurrently or in a cycled mode of flow where there is a duty cycle of infusion and removal periods. The duration of each period and any interval between can be selected to enhance heat and mass transfer with peritoneal tissue as well as maintain a desired volume of fluid in the peritoneal cavity. Also, the periods of infusion and removal can be synchronized with one or both of heart rate and respiration to optimize flow rates as well as heat and mass transfer with peritoneal tissue. For example, infusion can by synchronized with expiration and/or removal with inspiration. This allows embodiments of the invention to take advantage of the expansion of the peritoneal cavity that occurs during expiration to more readily infuse fluid into the cavity (due to decreased fluidic resistance) and also the contraction of the cavity that occurs during inspiration to assist in removing fluid from the cavity. In this way, embodiments of the invention can use the motion of respiratory cycles to assist and optimize the inflow and removal of fluids from the peritoneal cavity. This, in turn, requires reduced power for the pumping and removal of fluids resulting in a lighter weight hypothermic infusion system with extended operating life.

Also in various embodiments, the rate of hypothermic solution infusion, cooling rate and patient temperature can be titrated to treat specific medical conditions. For example, cooling rates and temperatures can be titrated to reduce the amount of coronary ischemic injury, or cerebral ischemic injury from myocardial infarction, cardiac arrest, stroke or other coronary/cerebral ischemic events; or to reduce an amount of ischemic tissue injury resulting to a tissue extremity. The cooling rates and temperatures can also be titrated to reduce the amount of inflammatory response from a surgical procedure such as a cardiovascular or neural surgical procedure.

Further details of these and other embodiments and aspects of the invention are described more fully below, with reference to the attached drawing figures.

BRIEF DESCRIPTION OF THE DRAWINGS

FIG. 2*c* is an elevation view illustrating various options for placement of a temperature sensor on the body.

FIGS. 4*a-b* are side and top views illustrating an embodiment of an access and infusion apparatus including an access device and infusion catheter advanceable through the access device.

FIGS. 5*f* and 5*g* are lateral views illustrating uses of an access port having a shearable tip.

FIGS. 7*a*-7*e* are lateral views illustrating uses of pressurized air to prevent tissue injury during catheter advancement.

DETAILED DESCRIPTION OF THE INVENTION

Figure 1:
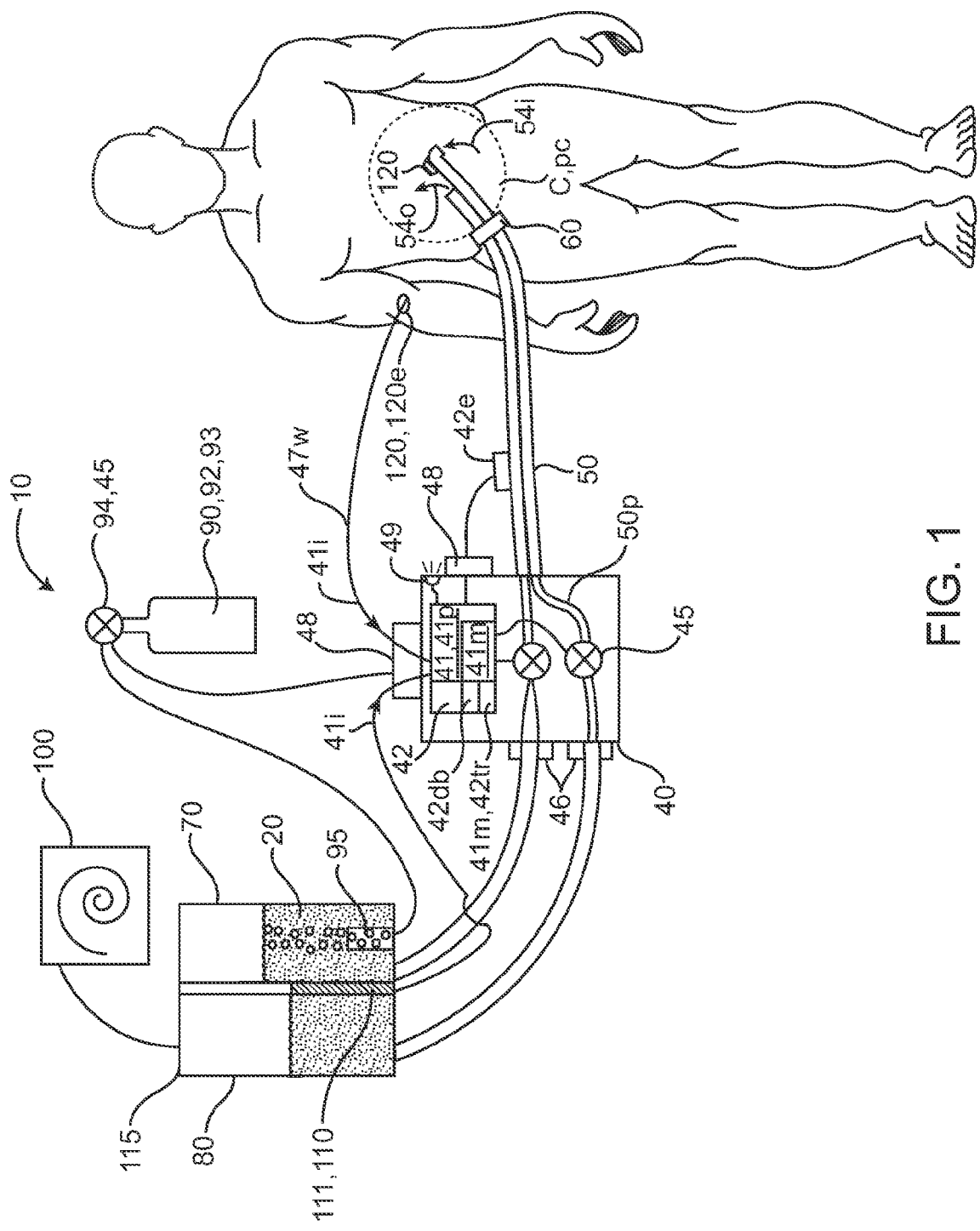
FIG. 1 is a schematic view illustrating an embodiment of a peritoneal hypothermia system.

Embodiments of the invention provide apparatus, systems and methods for providing therapeutic hypothermia through minimally invasive access to the peritoneal cavity. Many embodiments provide a system for providing hypothermia, resuscitation or other treatment in response to stroke, myocardial infarction, blood loss or any condition resulting in decreased perfusion to one or more locations in the body, including both internal organs and the extremities.

Referring now to FIGS. 1-5, an embodiment of a system 10 for the delivery of hypothermic or other fluid 20 to a peritoneal or other tissue cavity C which can comprise a main control unit 40, an infusion member 50 (also referred to herein as an infusion catheter), an access device 60, a fluid reservoir 70, a waste fluid container 80, a pressure source 90, a vacuum pressure source 100, a cooling device 110, and one or more sensors 120 such as temperature or pressure sensors. In various embodiments, system 10 can be used to deliver fluids to a number of body cavities such as the pleural cavity, vagina, intestines, nasal cavity and like structures, as well as to various vascular structures. Further fluid can be delivered for purposes of producing hypothermia, post hypothermic warming, hyperthermia, resuscitation, blood pressure management and other related treatments. However, for ease of discussion, system 10 will be referred to as a peritoneal circulation or hypothermia (PH) system 10 and cavity C will be the peritoneal cavity, however this is for illustrative purposes and it should be appreciated that other uses and application sites are equally applicable. For example, embodiments can be readily configured for use in the pleural cavity through selection of dimensions, shape, materials, etc.

Figure 2A:
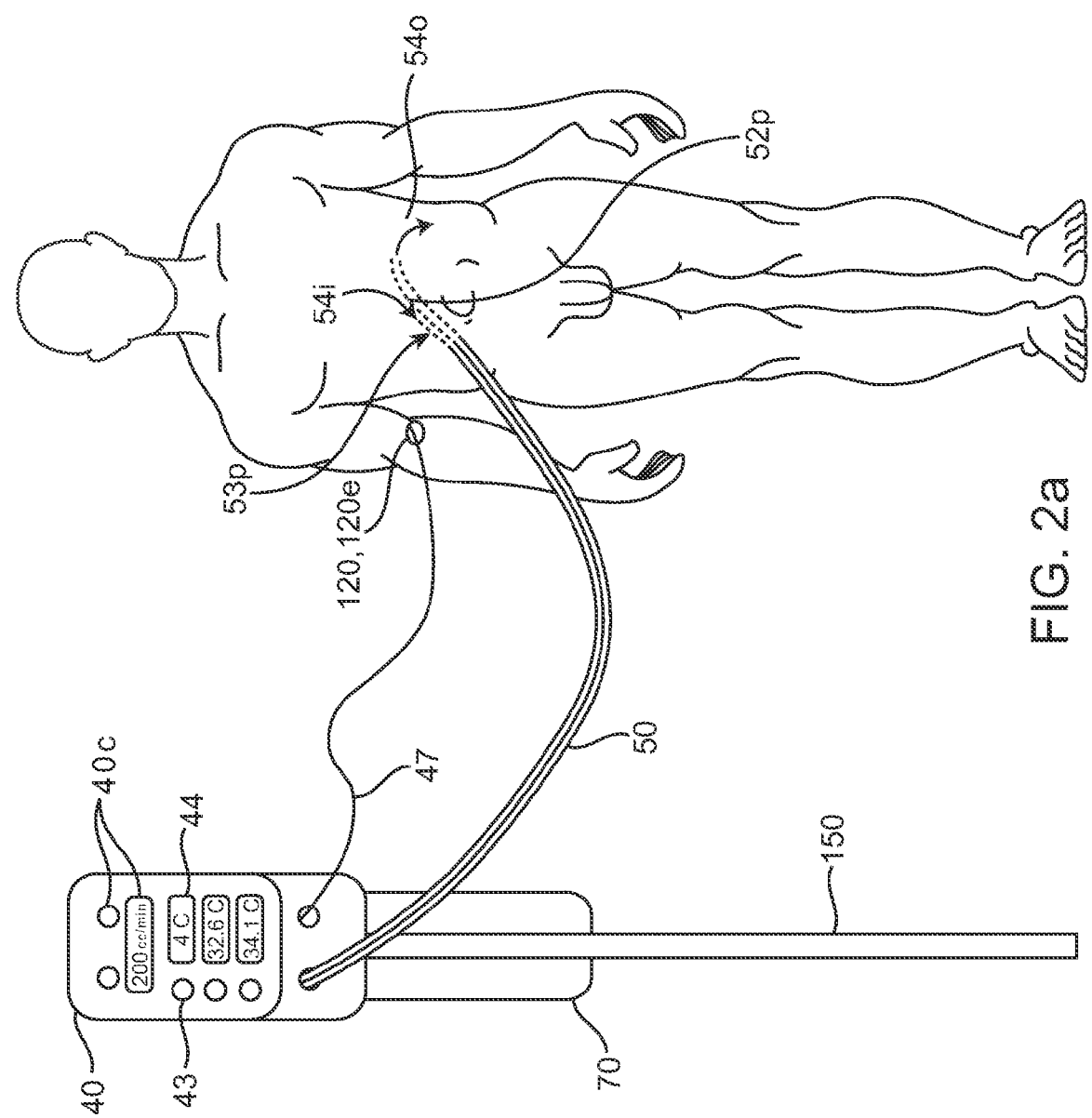
FIG. 2*a* is an elevation view illustrating an embodiment of the peritoneal hypothermia system applied to a patient with an infusion catheter and IV temperature sensor.
Figure 2B:
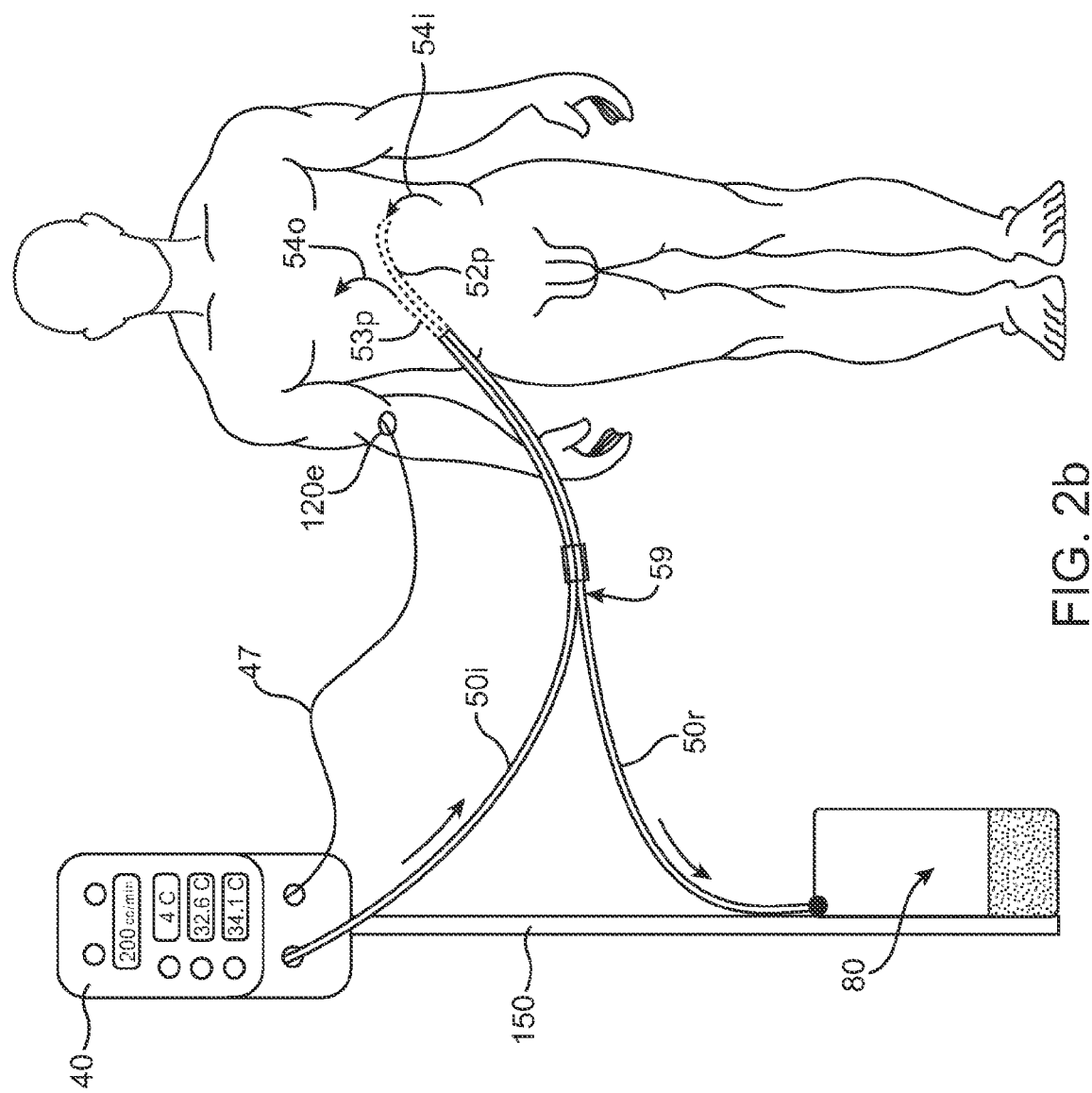
FIG. 2*b* is an elevation view illustrating an attached peritoneal hypothermia system having a separate outflow collection bag.

FIGS. 1, 2a and 2b show embodiments of system 10 in which multiple components of the system such as the control unit, reservoir, etc., are attached to an IV pole or other stand means 150. The proximal end of infusion catheter 50 is coupled to unit 40 and receives fluid 20 from an attached reservoir 70. The distal end of the catheter is positioned in the peritoneal or other cavity C of the patient so as to infuse fluid 20 into the cavity. A temperature or other sensor 120 is connected to the patient at an IV or other site to measure the patient's temperature. Pole 150 allows unit 40 to be placed at various locations around the patient and also provides a gravitation head pressure for delivery of fluid 20 into the patient. The pole 150 can be raised or lowered to provide greater or lesser amounts of head pressure, which can be sensed via means of a pressure sensor placed in infusion member 50. After the infusion catheter 50 is positioned at the desired body cavity site, the infusion (and removal) of fluid 20 can be initiated either under manual or automated control. The user can see various data (e.g., patient temperature) on displays 44 and make one or more adjustments using buttons or other user interfaces 43 or place the unit in an automated mode. Waste fluid can either be emptied into an external container, as the case in the embodiment in FIG. 2a, or into an integrated container 80 attached to pole 150, or another portion of the system. Preferably, waste container 80 and the connecting tubing are placed below the patient to provide for removal of fluid using gravitation head pressure alone (similar to reservoir 70, container 80 can be configured to be raised or lowered to vary the removal pressure). In such embodiments, the system can be configured so as to not require a pressure source 90 or vacuum source 100, but instead completely rely on gravitation head pressure alone for both functions. Such embodiments provide an increased measure of portability for field use since a pressure or vacuum source is required. Particular embodiments of this configuration can be further adapted for battlefield or other emergency medicine use through the use of one or more of light weight weather resistant components, power efficient and fault tolerant processors and circuitry, rechargeable high volume efficiency batteries (e.g., lithium or lead acid), and even the use of light weight manual pumping devices.

In various embodiments, fluid 20 comprises a solution 20 for the delivery of a medical treatment such as hypthothermic or resuscitative treatment. For ease of discussion, fluid 20 will be referred to as solution 20 or as infusate 20. Suitable solutions 20 can comprise various saline solutions (e.g., ringers lactate), various peritoneal dialysis fluids including nutritive based peritoneal dialysis fluid (e.g., those containing dextrose and other sugars), and fluorocarbon solutions configure for oxygen transport and artificial blood solutions known in the art. For aqueous embodiments, the solution can also include one or more freezing point depression compounds (e.g., NaCl) allowing the solution to be cooled below the freezing point of water to allow for faster cooling when so desired.

Also, solution 20 can contain one or more medicaments for treatment of myocardial infarction, cardiac arrest or other severe cardiac condition, stroke, shock, reperfusion injury or other medical conditions. Specific families of medicaments can include vasoconstrictors, hemolytic compounds (e.g., TPA, streptokinase and like compounds), anticoagulants, coagulants, calcium channel blockers, antibiotics, manitols. Also in specific embodiments, solution 20 can be configured to have resuscitative effects for treatment of heart attack, stroke, or severe blood loss. It can also have various agents known in the art for treatment of reperfusion injury. The delivered amount of a particular medicament can be titrated to the patient's weight and condition with titration controlled manually or by a drug delivery module resident within controller 41. Also, the dose of particular compounds can both be delivered as a bolus with the initial bolus of hypothermic solution and also on a continuous basis. The delivery rate of a particular medicament or group of medicaments can also be controlled responsive to the patient's temperature, blood pressure, heart rate or other vital sign monitored manually, by system 10, or by other monitoring means.

Solution 20 can also comprise oxygenated solutions such as oxygenated flourocarbon solutions that can be configured to deliver sufficient oxygen to tissue (by gas exchange with peritoneal or other surrounding tissue) to at least partially meet the oxygen demands of the body. Flourcarbon solutions 20 can be pre-oxygenated or can be oxygenated in reservoir 70 or outside of it using oxygen gas sources described herein. Solution 20 can also include contrast media to allow for imaging by x-ray, MRI, ultrasound, and other imaging modalities known in the art.

This main control unit 40 will typically comprise logic resources 41, memory resources 42, user interface devices 43, displays 44, control valves 45, fluid connections 46, electrical connections 47, data input/output ports/interfaces 48, and audio output devices 49 (e.g., a speaker). The unit can be contained in a frame or housing 40f and will frequently include a handle 40h for portability which can be disposed at any point on frame 40f. While unit 40 can be a stand alone unit, it can also be configured to be readily attached to other components of system 10, such as reservoir 70, waste container 80, and pressure source 90 as is discussed herein.

Displays 44 and user interfaces 43 can comprise a console face or console device 40c. Console face 40c can be permanently attached to unit 40; however it may be pivotal in multiple directions to allow viewing from different angles. In particular embodiments, it may also be removable, functioning as remote console 40rc that wirelessly communicates with unit 40. In use, such wireless embodiments allow the user to operate the system from any position around the patient, or even to do so remotely. This provides the user with greater flexibility and ease of use in both setting up and operating the system, including faster response time in making system adjustments. For example, if the user sees that the patient requires immediate attention due to fallen blood pressure, blood oxygen saturation, etc. or even cardiac arrest, they can make an immediate adjustment to the system using the remote console rather than having to rush to reach the control unit.

In many embodiments, logic resources 41 can be configured as a controller for controlling one or more parameters related to a hypothermic or other treatment regimen, for example, infusate temperature, body temperature, infusion and removal rates, infusion and removal pressures, total volume infused and removed and like parameters. For ease of discussion, logic resources 41 will now be referred to as controller 41; however, it should be appreciated that logic resources 41 can be configured to perform a variety of operations including communicating with external devices including devices linked over the Internet; data operations; and various power management functions.

Controller 41 can include one or both of analog or digital circuitry for performing it's control operations. Controller 41 will also typically be configured to receive one or more inputs 41$i$ from sensors 120, pressure source 90, and control valve 45. Typically, controller 41 will include a computer processor 41$p$ which is configured to execute one or more electronic instruction sets contained within a software module or module 42$m$, which can be stored in memory resources 42 or controller 41. Additionally, controller 41 can be configured to be programmed by the user (e.g., using unit 40 or by an external device such as a wireless device) to allow for manual control of one or more operations of system 10 (e.g., infusion rate). Processor 41$p$ can be an off the shelf processor (e.g., such as those available from INTEL Corporation), or can be a custom designed ASIC.

System 10 can include a number of modules 42$m$ which can be configured to control a variety of operations relating to the use of system 10, for example, temperature control of the infused solutions as well as that of the patient, flow and pressure control of the infused and removed solutions, the level oxygenation of the infused solution and control of like operations. Modules 42$m$ may employ algorithms to interpret sensed temperature data to control fluid flow such that the core temperature of the patient may be maintained at the desired level. In particular embodiments, modules 42$m$ can control the delivery of solution 20 to achieve or enhance a particular medical treatment, such a hypothermic treatment. For example, a module 42$m$ can control the infusion of solution 20 to enhance the thermal and/or gas exchange of the solution with peritoneal tissue for a hypothermic and/or resuscitative treatment. This can be achieved by controlling the infusion of the solution to control the temperature and pressure within the peritoneal or other tissue cavity.

Memory resources 42 can comprise one or more of ROM, RAM, DRAM and various non-volatile memories including EPROMs and flash memory. In addition to module 42$m$, memory resources 42 can also include a database 42$db$, which can include one or more treatment regimens 42$tr$, such as hypothermic treatment regimen for a particular medical condition (e.g., stroke) and/or a particular patient population (e.g., pediatric vs. geriatric). User interfaces 43 can comprise, buttons, keypads, pressure sensitive finger pads, touch screens and like devices. Control valves 45 can include various electronic control valves known in the art and are controlled by controller 41.

Fluid connections 46 can include luer lock or other fluidic connections known in the art and can be configured to be coupled to one or more of infusion member 50, reservoir 70, container 80, pressure sources 90 and vacuum source 100. They may also be snap fit and/or quick disconnect so that the user can quickly reattach a different infusion member, pressure source, etc. They may also be color coded for the particular connection (e.g., one color for an infusion line, another for removal, etc.). They can also have integrated control valves 45 and/or sensors 120, the latter being configured to alert the user when the connector has become disconnected or is otherwise not fully connected.

Electrical connectors 47 can be configured to be coupled to one or more wires 47$w$ for coupling to sensors 120, a remote controller or other like devices. Data input/output ports or connections 48 can include those known in the portable and computer arts including PCMCIA connections and UART connections. They can also include various wireless interfaces/connections including Rf connections configured for BLUE TOOTH protocol and infrared interfaces. In specific embodiments, I/O connections 48 can be configured to interface with an external flash memory or other external memory device 42$e$ coupled to infusion member 50 or another component of system 10. This allows control unit 40 to upload and run one or more modules 42$m$ stored in flash memory coupled to infusion catheter 50. In use, such embodiments reduce the memory requirements of control unit 40, and also serve to improve reliability by not relying on a single memory device which may become compromised. Thus, the user need only swap out an infusion catheter 50 (other component of the system carrying a memory device) rather than swapping out a whole control unit 40.

Wireless I/O ports 48 can also be configured to wirelessly communicate with sensors 120 and control valves 45, one or both of which can include RFID tags. In use, such embodiments reduce the number of connecting wires required by the system, making it easier for the medical personnel to position components to the needs of the patient and the scene, rather then tethering the equipment around the patient. It also allows the user to quickly reposition a temperature or other sensor 120, without having to stop to disconnect and reconnect the sensor.

Sensors 120 can be configured to measure a variety of physical properties related to the use of system 10. Accordingly, they can comprise a variety of biomedical sensors known in the art, including temperature sensors, pressure sensors, force sensors, flow sensors, pH sensors, oxygen and other gas sensors (e.g., $CO_2$), acoustic sensors, piezoelectric sensors, and the like. Suitable temperature sensors can include thermisters, thermocouples, optical sensors, and like devices. Suitable pressure and force sensors can include strain gauges, solid state, and mems based strain gauges. Suitable flow sensors include electromagnetic flow sensors and aneometric flow sensors known in the art. Temperature, pressure sensors and flow sensors positioned on infusion member 50 and include one more miniature thermisters, and solid state pressure sensors and flow sensors known in the art. One more sensors 120 can also include RFID tags or like devices so as to be able to wirelessly signal an input to controller 41 or another instrument.

A discussion will now be presented of infusion catheter 50. In various embodiments, infusion catheter 50 can be configured to be positioned in the peritoneal PC or other tissue cavity C and deliver fluid to the cavity for a hypothermic or other medical treatment discussed herein. Typically the infusion member will be advanced through an access device 60 which is inserted to a controlled depth into the abdominal or other tissue wall. The infusion catheter can be configured to be advanced by itself or through use of an advancement member 30 discussed herein which can be reversibly positioned in a lumen of the infusion member and acts to increase the pushability or column strength of the infusion member when so positioned.

In many embodiments, infusion member 50 will comprise a catheter, so for ease of discussion, infusion member will now be referred to as catheter 50. The catheter can have a length ranging from 20 cm to 200 cms to allow for connection to unit 40 at varying distances from the patient. Smaller lengths can be used for pediatric application. The outer diameter 50D of the catheter can be sized for advancement through standard surgical port access devices and in varying embodiments, can range from about 0.1 to 1 inch though other sizes are also contemplated depending upon the target tissue site. For example, smaller sizes can be used for accessing the pleural cavity as well as for pediatric applications. Various embodiments of the catheter can include insertion depth indicia 50di and or radio-opaque/echogenic markings 50m in order to assist in determining insertion depth either visually or under image guidance (e.g., fluoroscopy, ulstrasound, etc.).

Catheter 50 can include at least one lumen 51, extending all or a portion of its length 50L. Typically, the catheter will include at least a first lumen 52 for infusion of infusate 20 and a second lumen 53 for removal of fluid, though additional lumens are also contemplated. Typically, the lumens will be round or oval shaped, but can also be D-shaped or crescent shaped. In various embodiments, the inner diameters 52id and 53id of lumens 52 and 53 can range from about 0.05 to about 0.5 inches though other diameters are also contemplated. Desirably, lumen 52 has a sufficient inner diameter 52id to be able to infuse 2 to 4 liters of hypothermic infusate 20 to reduce the patient's body temperature by at least about 3° C., or more preferably, ten minutes or less via heat exchange with peritoneal tissue using pressures less than 3 atmospheres and more preferably less than 1 atmosphere. Diameter 53id is also desirably configured to deliver between 2 to 4 liters of infusate 20 in ten minutes or less. Diameter 53id can be configured to remove similar volumes of fluid in similar time periods. In addition to fluid infusion and removal, one or both lumens 52 and 53 can be sized for advancement of an advancement member, guidewire, endoscope or other viewing device, a sensing member, tissue biopsy device, or other minimally invasive surgical device.

In preferred embodiments, infusion lumen 52 will extend the entire length of the infusion catheter. The removal lumen 53 is desirably not continuous to the very tip of the infusion catheter to allow for an advancement member 30 (described herein) to have a surface to push against so as to advance the infusion catheter. Alternatively, the inner diameter 53id of removal lumen 53 can neck down near the distal end of the infusion catheter so as to be able hold the advancement member by an interference fit.

In a preferred embodiment, lumens 52 and 53 are contained in a single catheter 50 for it's entire length such as in a single dual lumen catheter. However, in various embodiments, the catheter 50 can split up a point 59 into separate portions 50i and 50r containing the infusion and removal lumens to provide for easy connection to reservoir 70 and waste container 80 as is shown in FIG. 2b. Also, the distal infusion and removal portions 52p and 53p can extend different lengths. In FIG. 2a, portion 52p can extend past portion 53p as discussed in further detail herein. FIG. 2b illustrates a reverse configuration.

Figure 3A:
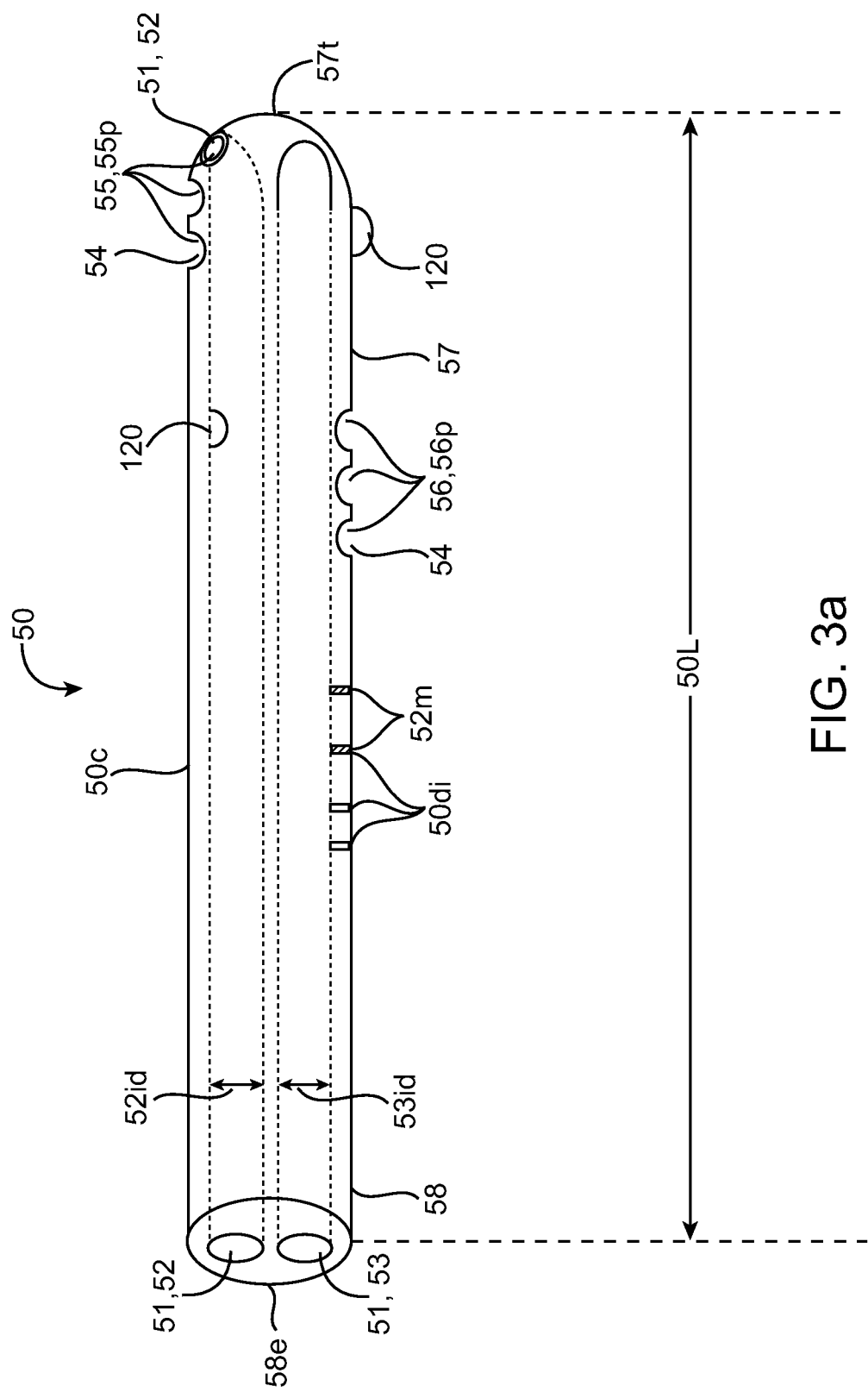
FIG. 3*a* is a lateral view illustrating an embodiment of the infusion catheter.
Figure 3B:
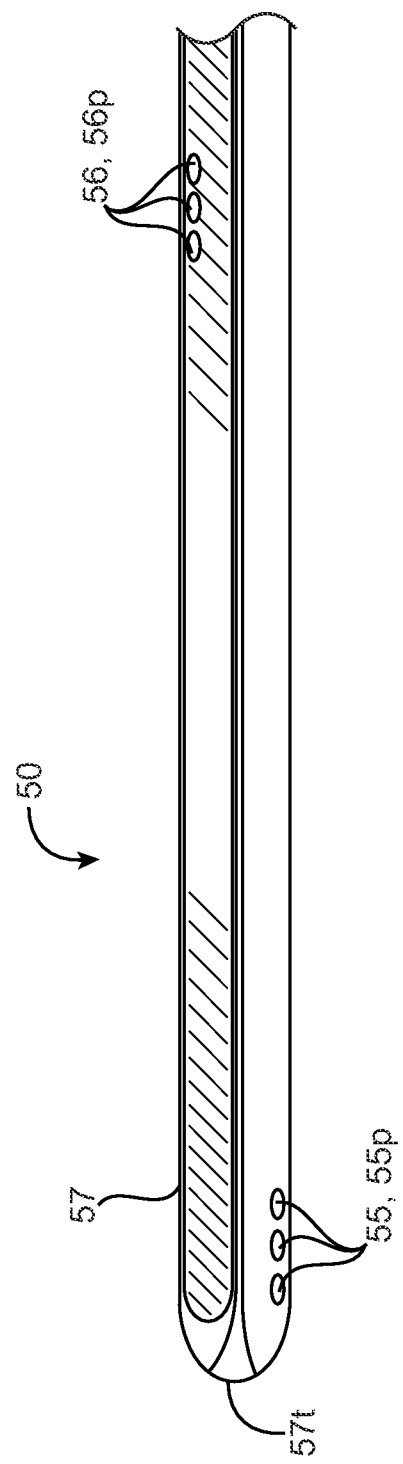
FIG. 3*b* is a lateral sectional view illustrating the distal portion of an embodiment of the infusion catheter having infusion and removal apertures positioned to reduce clogging by peritoneal tissue.
Figure 3C:
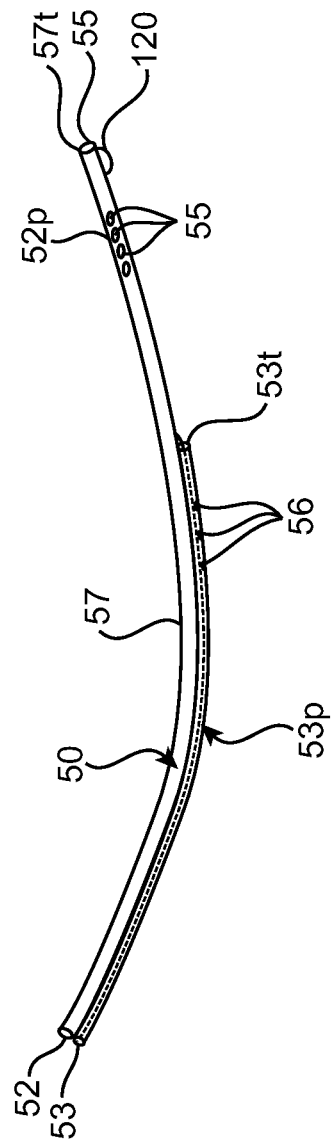
FIG. 3*c* is a lateral sectional view illustrating the distal portion of embodiment of the infusion catheter having a longer length for its infusion lumen than its removal.
Figure 3D:
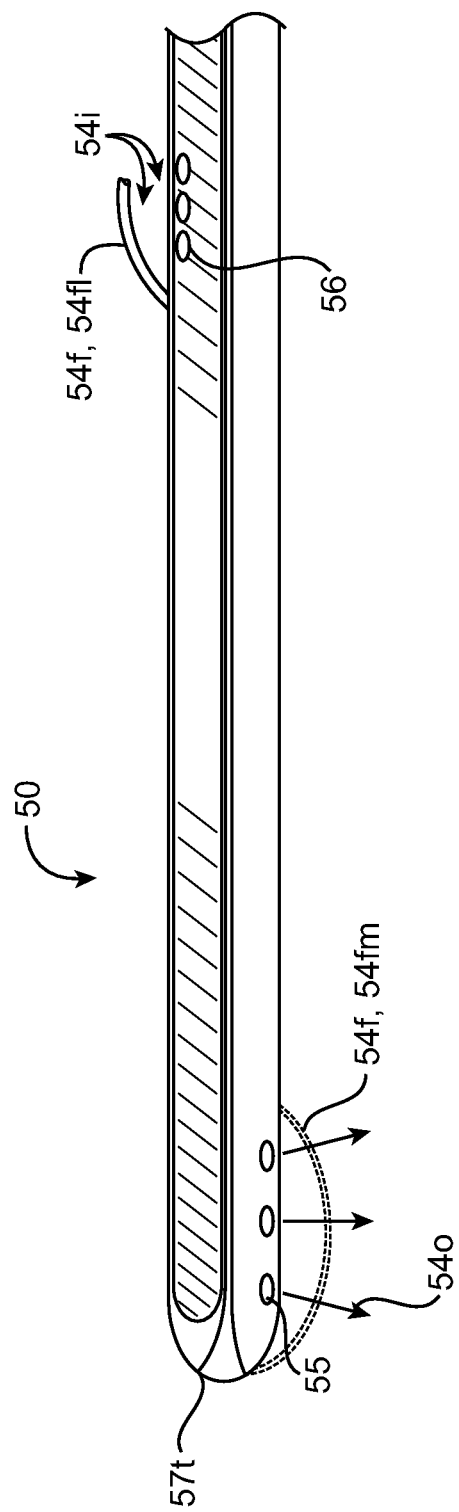
FIG. 3*d* is a lateral sectional view illustrating the distal portion of an embodiment of an infusion catheter having infusion/removal apertures with features to reduce to clogging by peritoneal tissue.
Figure 4C:
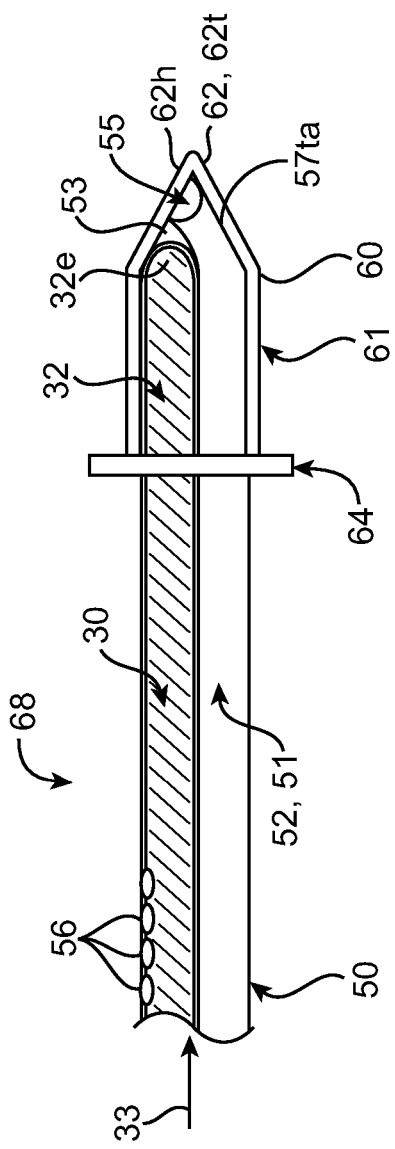
FIG. 4*c* is a sectional view illustrating the distal portion of an access and infusion apparatus having an advancement member for advancing the infusion catheter.
Figure 4D:
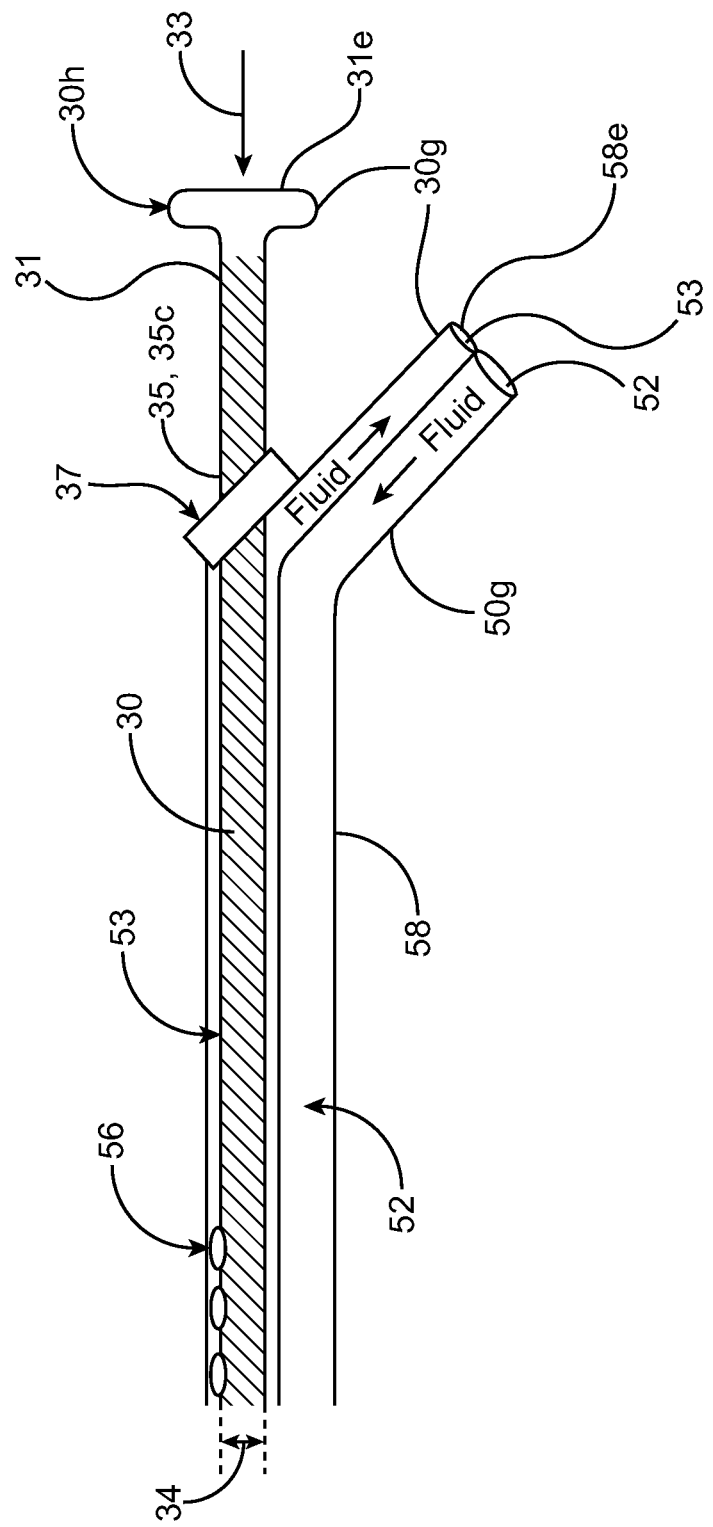
FIG. 4*d* is a sectional view illustrating the proximal portion of an access and infusion apparatus having an advancement member with a handle for advancing the infusion catheter.

Catheter 50 will also typically include one or more apertures 54 positioned along catheter distal portions 57 for the outflow 54o and inflow 54i of fluid to provide for the infusion and removal of fluid from the peritoneal or other cavity C. Typically, the outflow or infusion apertures 55 will be placed more distally than inflow or removal aperture 56 to reduce the pressure for removal, and reduce the immediate uptake of the infused solution by removal apertures 56. Both types of apertures can be positioned in patterns 55p and 56p to reduce clogging by peritoneal tissue and improve flow rates in both directions. Typically, this involves a minimal amount of spacing between each aperture (e.g. 1 mm or greater). Further resistance to the tissue clogging of outflow and inflow apertures 55 and 56 can also be achieved by moving at least some of the outflow apertures off of tip 57t and placing the inflow aperture even more proximally with respect to the catheter tip (for example, several centimeters or more) as is shown in FIG. 4b. In preferred embodiments, this can also be achieved by extending the portion 52p of the catheter containing infusion lumen 52 several centimeters more distally than the catheter portion 53p which contains removal lumen 53 as is shown in FIGS. 2a and 3c. The transition 53t between the two portions is desirably tapered to provide for smooth advancement of the catheter. In still other embodiments, one or both sets of apertures 55 and 56 can include protective features 54f such as a protective porous membrane 54fm, surrounding the apertures 56 or a protective lip or baffle 54fl overlying at least a portion of apertures 55 as is shown in FIG. 3d. The lip or baffle 54fl is desirably configured to direct away tissue encroaching from the distal direction, but still allow inflow from the proximal direction. These features can be placed on either sets of apertures 55 and 56.

Catheter 50 will typically include one or more sensors 120 which can be selected to measure: flow rates, pressure, temperature or other physical property. In preferred embodiments, the catheter will include at least one temperature sensor positioned on the distal portion or even the distal tip 57t of the catheter to measure temperature within the peritoneal or other cavity. The input from temperature sensor 120 can be utilized by controller 41 and/or a thermal regulation module 41m to regulate infusate flow rate and the infusate temperature, so as to reduce the patient's temperature a selected amount as part of a hypothermic treatment regimen. Multiple temperature sensors may be placed at various locations on the catheter to obtain a composite temperature over a volume of the peritoneal or other cavity. Temperature sensors 120 can also be placed within lumens 55 and 56 to monitor the temperature of infused and removed fluid.

In addition to temperature sensors 120 placed on catheter 50, various external temperatures sensors 120e may be placed in one or more locations in body. FIG. 2c illustrates the various placement options for temperature sensors 120e which can in some embodiments be wireless based sensors known in the art. Such placement options can include peritoneal PC, intravascular I, auricular A, oral O, epidermal ED and rectal/urethral RU. In preferred embodiments, peritoneal and/or intravascular temperature can be used for control purposes. However, in various embodiments, temperatures can be sampled from multiple locations and a composite temperature can be developed and used for control purposes, with assignable weightings to each location. In use, a composite measurement can give a more accurate reflection of the patient's temperature particular during fast cool regimens. In these embodiments, a temperature map can be developed and displayed to show the progress of cooling over the patient's body (e.g., as a wave or depth of cooling). In other embodiments, only temperature measurements from a particular target site to be cooled can be used, e.g., the peritoneal cavity.

Catheter 50 can also include at least one flow sensor 120 positioned in lumen 55. Flow sensors 120 positioned in lumen 55 can be configured to perform several functions. First, to provide an input to controller 41 for controlling infusate flow rate. Second, to provide an input to the controller indicating the entry of the distal tip of the catheter into the peritoneal or other tissue cavity so as to minimize the risk of injuring a peritoneal organ or other tissue. This latter function can be achieved through use of entry point detection module 41 which detects entry by an increase in infusate flow rate which occurs when the tip of the catheter emerges into the peritoneal cavity and one or more infusion apertures become patent. In such embodiments, the pressure source 90 can be configured to provide at least a minimal pressure to the infusion lumen during catheter advancement for purposes of detecting flow. Entry can be detected by an absolute increase in flow rate or a rate of increase or a combination of both (i.e. analogous to PD control). Once entry is detected, controller 41 can send an audio alarm signal to audio output device 49 to alert the user that entry has occurred. In one embodiment, a series of pre-alarm signals may also be sent indicating when the entry point is close (e.g., one aperture has entered the cavity) so as to provide the user with more advance warning of entry.

Catheter 50 can also include one or more pressure sensors 120 positioned at various locations on or within the catheter. In particular embodiments, pressure sensors 120 can be positioned in lumen 55 to detect entry of infusion catheter into the peritoneal or other cavity, as described above. However, in this case, entry is detected by a decrease in pressure either absolute or rate of decrease. In another application for the use of pressure sensors, the pressure sensor 120 can be positioned on a distal portion of the catheter, such as tip 57t to detect the pressure in the peritoneal or other cavity C. This pressure signal can then be utilized by controller 41 to decrease or shut off infusion when the measured peritoneal cavity pressure exceeds a selected absolute threshold or rate of increase. The controller can also send an accompanying alarm signal to speaker 49. Desirably, the controller is configured to slow down the infusion rate as the selected pressure threshold is reached rather than shutting off infusion altogether. In use, such embodiments prevent or reduce the likelihood of over-pressurizing the peritoneal cavity. They also serve to optimize the rate of patient cooling (since the system need not be shut off to respond to over pressurization events) and allow the system to be run in a more automated fashion with less oversight by the user.

Catheter 50 can be fabricated from various biocompatible flexible polymers known in the art such as polyethylene (HDPE and LDPE), silicone, polyurethane, PTFE, PEBAX and like materials. All or a portion of the catheter can include a lubricous coating 50c such as a silicone coating to assist in advancement of the catheter through tissue. Also, the tip 57t or distal portions 57 can be tapered. The catheter can also include braiding or other means for improving kink resistance and increasing the burst strength of the catheter lumens. In particular embodiments, the proximal portions 58 of the catheter can be braided or otherwise stiffened such that the catheter has sufficient column strength to be advanced into the peritoneal cavity through manipulation of the proximal portion 58. In some embodiments, the catheter can include a handle (not shown) positioned at proximal end 58e of the catheter to assist in advancement of the catheter.

In many embodiments, infusion catheter 50 is configured to be advanced into a tissue cavity through use of an access device 60. Access device 60 is configured to penetrate a selectable distance D through the skin S and into sub-dermal tissue layers SDL. The infusion catheter 50 is then advanced through a lumen of the access device into the peritoneal PC or other cavity C as is described herein. In this respect, access device 60 functions as a port for the introduction and advancement of infusion member 50 into tissue. Collectively, infusion catheter 50 and access device 60 can comprise an access and infusion apparatus 68 which can be sterily packaged as a kit separate from other components of system 10, such that the apparatus can be readily stored and transported separate from unit 40 or 140. This helps to maintain the sterility of the entire system. The catheter and access device of apparatus 68 are sized to be used together so that the user need not match the size of the catheter to that of the access device. However, other embodiments are contemplated where the catheter and access device are packaged separately so they can be mixed and matched. In the later case, matching infusion catheters 50 and access devices 60 can be color coded for ease of matching.

In various embodiments, access device 60 will typically include at least one lumen 61 extending there through and a tissue penetrating distal end 62. Lumen 61 can have an inner diameter 61D sized to accommodate a variety of different sized infusion catheters 50 and in various embodiments can range from about 0.1 to 0.5 inches, though other sizes are also contemplated. Access device 60 can be a surgical port device, trocar or other surgical access known in the art. Access device 60 will typically have a stop 64 to control the penetration depth of the access device into the tissue so that user does not need to precisely control the insertion depth. Stop 64 can comprise a flange or lip that protrudes from the outer walls of the access device and is positioned close to proximal end 63. Stop 64 can also include an adhesive 65 and/or a suture opening 66 for affixing the access device to the skin surface once it is inserted. Desirably, adhesive 65 has sufficient adhesive force and area to laterally stabilize the access device on the skin surface. The stop 64 can also be adjustable (e.g., using screws or an indexing mechanisms) to control the penetration depth D of the access device into the tissue. In preferred embodiments, the access device is configured to penetrate into sub-dermal tissue layers SDL, but not completely through abdominal or other tissue wall TW. The access device can be fabricated from various biocompatible rigid polymers and metals known in the art, it can also include indicia along it's length indicating penetration depth.

Figure 5B:
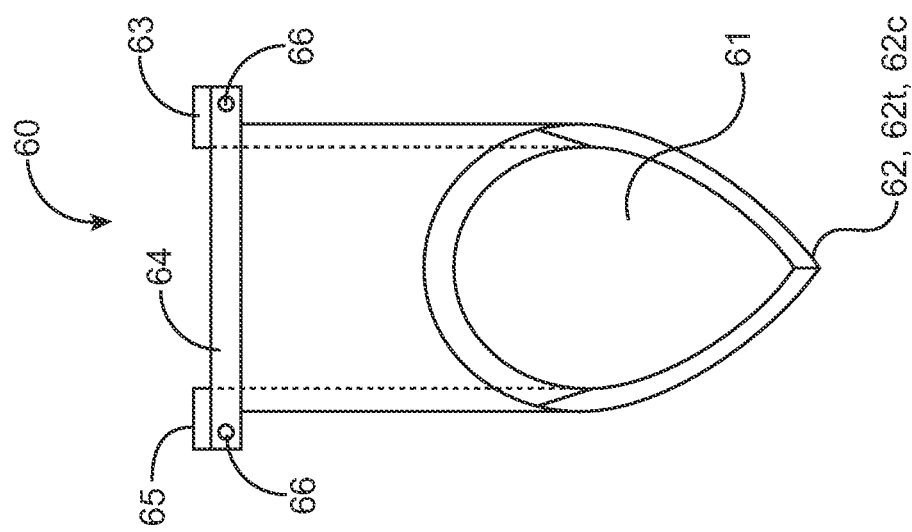
FIGS. 5*a*-5*b* are lateral views illustrating an embodiment of an access port having a trocar tip.
Figure 5A:
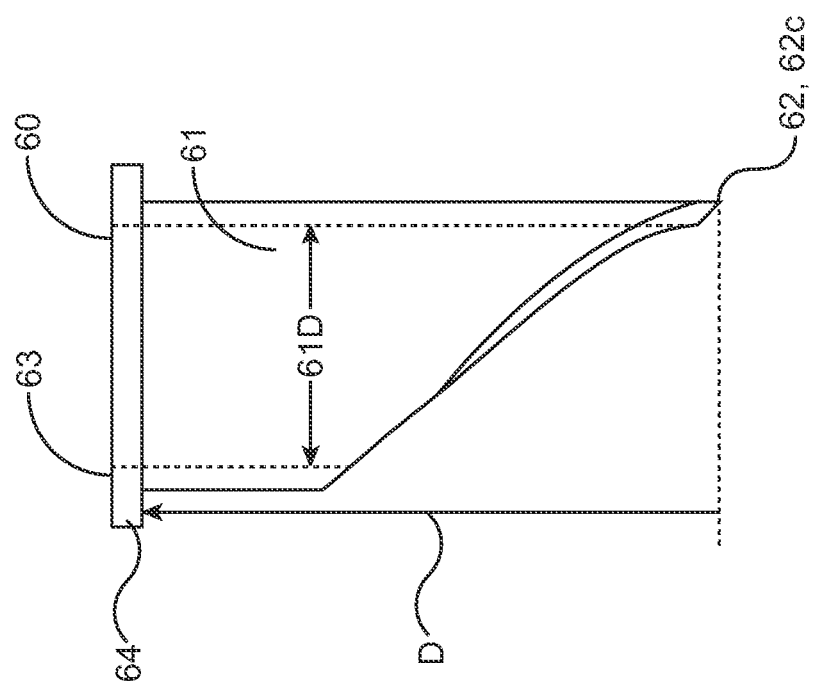
Figure 5E:
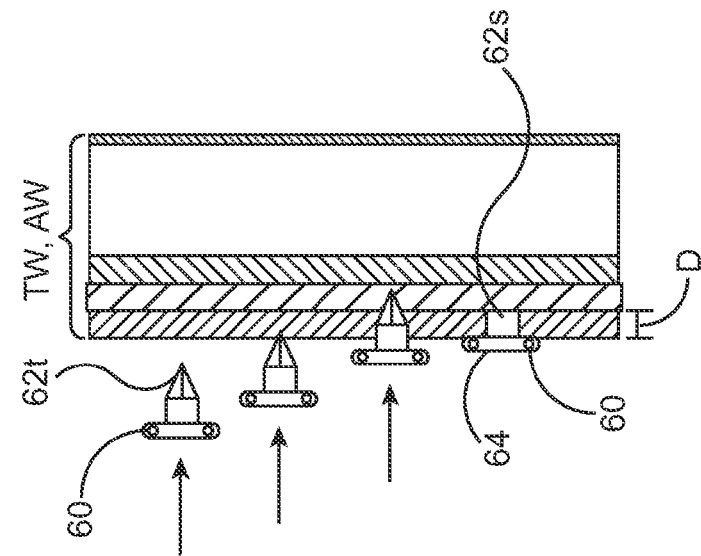
FIGS. 5*d* and 5*e* are lateral views illustrating uses of embodiments of an access port having a hinged tissue tip (FIG. 5*d*) or a retractable tissue penetrating tip (FIG. 5*e*.).
Figure 5C:
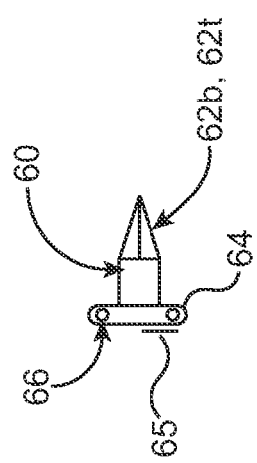
FIG. 5*c* is a lateral view illustrating an embodiment of an access port having a hinged tip.
Figure 5D:
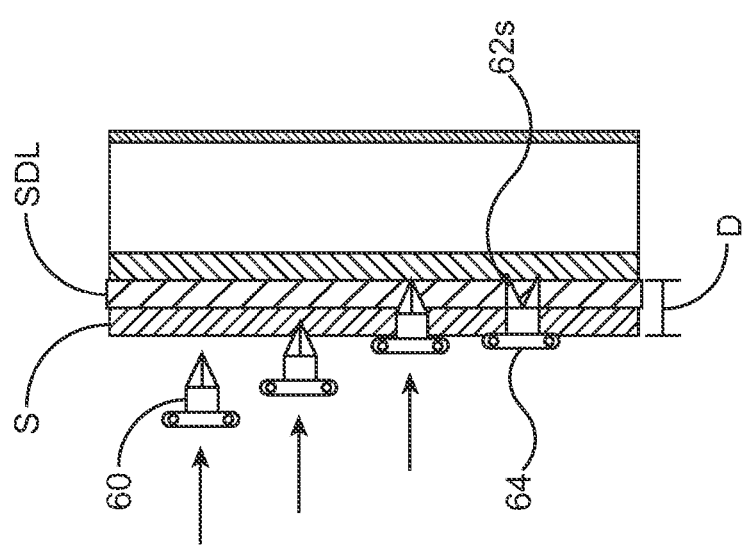
Figure 6A:
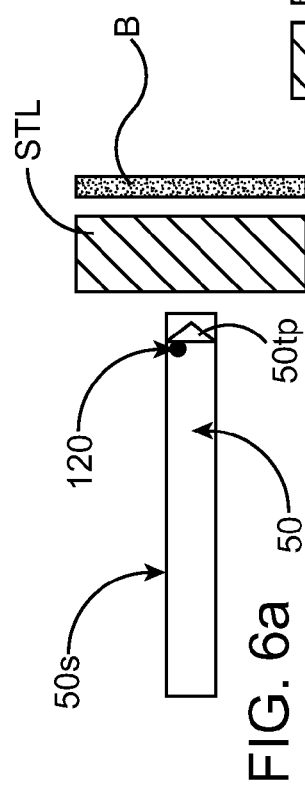
FIGS. 6*a*-6*e* are lateral views illustrating use of an embodiment of an infusion catheter having a protective sheath.
Figure 6B:
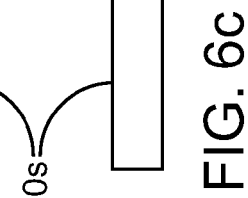
Figure 6C:
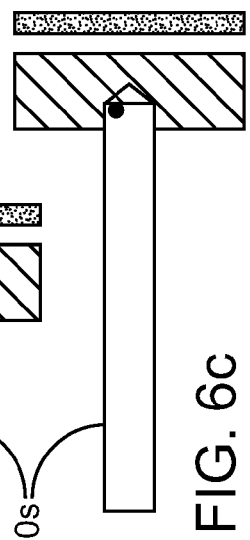
Figure 6D:
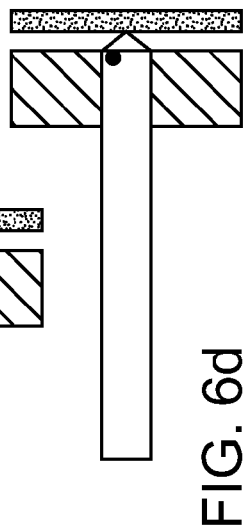
Figure 6E:
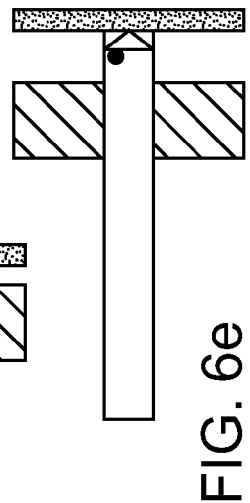

Tissue penetration tip 62 can have a variety of tissue penetrating shapes including a trocar tip shape 62c as is shown in FIGS. 5a-5b. In many embodiments, the distal end 62 of access device 60 can also be transformable from a tissue penetrating configuration 62t to a non-tissue penetrating 62s or safety configuration. This can be achieved through a variety of means. For example, in one embodiment, the distal end can be hinged as is shown in FIG. 5c and 5d such that once the access device reaches it's stop depth, advancement of the infusion catheter forces the hinged blades 62b open or through a spring-loaded mechanism which provides for the blades to spring away from the lumen once an appropriate amount of incision has been achieved. In another embodiment shown in FIG. 5e, the distal end can be retractable through use of spring loaded or like mechanism. In another embodiment shown in FIGS. 5f-g, distal tip 62 of access device 60 can be a shearable tip 62h, for example by advancement of catheter 50, such that the catheter 50 breaks through tip 62 and once sheared, renders it a blunt non-tissue penetrating tip now in the safety configuration. Distal tip 62 can be configured to be shearable through the use of notching or other weakening features or treatment or through the use of dimensioning (e.g., wall thickness) to more readily shear when an axial force is applied by catheter 50 and/or advancement member 30. In another embodiment (not shown), access device 60 can be put into the safety configuration through the use of an overlying slidable sheath that slides over device 60 once the penetration depth is achieved through use of stop 64 or other penetration limiting means.

Infusion catheter 50 can be advanced into tissue by different means. As described above, in some embodiments, the catheter can have sufficient column strength to advance into tissue by manipulation of a proximal portion of the catheter without any additional support. In these embodiments the catheter tip is configured to be tissue penetrating, without external support. However, in preferred embodiments, the catheter is configured to advance through means of advancement member 30 which is removably positionable in at least one of the lumens 51 of infusion catheter 50 to advance the catheter in a distal direction 33 through the abdominal or other tissue wall. In these latter embodiments, catheter tip 57t is tissue penetrating when supported by advancement member 30, but upon removal of the advancement member, the tip becomes a substantially atraumatic tip 57ta. This can be facilitated by constructing the catheter tip from flexible polymer material as well as tapering the tip. The use of an atraumatic tip 57ta allows the user to continue to advance the catheter 50 into the peritoneal or other cavity C in order to position apertures 55 and 56 at a desired location as well as take temperature readings in multiple locations without risk of injury to the peritoneal organs. It also allows the catheter to be readily repositioned without risk of similar injury.

In many cases, the advancement member will be sized for advancement in the removal lumen 53 or other lumen besides infusion lumen 52 so as to allow for the infusion of solution 20 through the catheter during catheter advancement to detect entry of the catheter tip into the peritoneal cavity using techniques described herein. While in many cases it will be sized to be removably positioned in catheter 50, in other embodiments it can also be fixed in position within the catheter.

Desirably, the advancement member has sufficient column strength to advance infusion catheter 50 through the abdominal wall AW or other tissue TW and into the peritoneal PC or cavity C by manipulation of a proximal portion 58 of the infusion member or a proximal portion 31 of the advancement member. In addition to having sufficient column strength to advance the infusion member, the advancement member can also be configured to be able to have sufficient column strength to push through or shear embodiments of access device that have a shearable distal portion 62h.

In preferred embodiments, the advancement member can have a handle or grip 30h positioned at its proximal portion 31 to facilitate manipulation by the user. In an embodiment shown in FIG. 4D, the handle 30h can be configured along the proximal portion of catheter 50 to having gun like grip 30g allowing the user to hold the catheter by grip 30g and advance the advancement member in a distal direction 34 using only their thumb. In such embodiments, the proximal portion 58 of the catheter can be directed downwards forming a gun-like handle shape 50g that can be held in the user's hand.

As described above, the advancement member will be positioned in the removal lumen 53 of the infusion catheter so as to allow for flow of solution 20 through the infusion lumen 52 during advancement of the infusion catheter. In order to prevent fluid from leaking out of the removal lumen in the space between the removal lumen walls and the advancement member, the infusion catheter can have an adjustable valve 37 positioned around the advancement member to form a fluidic seal around the advancement member during movement of member 30 or when stationary. In a preferred embodiment, valve 37 can comprise a Touhy-Borst type adapter known in the art and include a single or a multi arm adapter to allow for multiple connections (e.g., to waste container 80 as well as to one or more biomedical monitoring instruments).

Valve 37 can also be configured to fluidicaly seal the proximal end of the removal lumen when the advancement member is not in place. Adjustable valve 37 can be configured to not only form a fluidic seal around the advancement member but also to hold the advancement member in place within infusion catheter. This allows the user to selectively position the advancement member in the infusion catheter during advancement of the latter. This positioning in turn can allow the user to select the amount of flexibility or stiffness of the distal portions of the infusion catheter.

The advancement member can have a variety of lengths depending upon the application and the length of infusion catheter 50. In preferred embodiments the advancement member has a length such that the proximal end 31e of the advancement member extends past the proximal end 58e of the infusion member (when fully inserted into the infusion member) so that proximal end of the advancement member can be readily manipulated by the user. The diameter 34 of the advancement member is sized such that it can be readily advanced or withdrawn from the infusion member with minimal or in some cases slight resistance. In other cases, member diameter 34 can be sized to have some resistance with lumen 53 of infusion catheter or even to result in an interference fit within the lumen.

In various embodiments, the advancement member can be fabricated from various biocompatible metals such as stainless steal or rigid polymers known in the art (PEEK, polyamides, polyimides, polyetherimide and like materials). The material of the advancement member together with it's diameter are desirably selected to meet column strength described above. The material for the advancement member can also be selected to have a lubricous surface 35 or be coated with a lubricous coating 35c, such as silicone or TEFLON, to facilitate advancement of the advancement member in the infusion catheter. Additionally, all or a portion of the advancement member can comprise a radio-opaque material (including a distinct marking) for visualization under various medical imaging modalities.

Figure 2D:
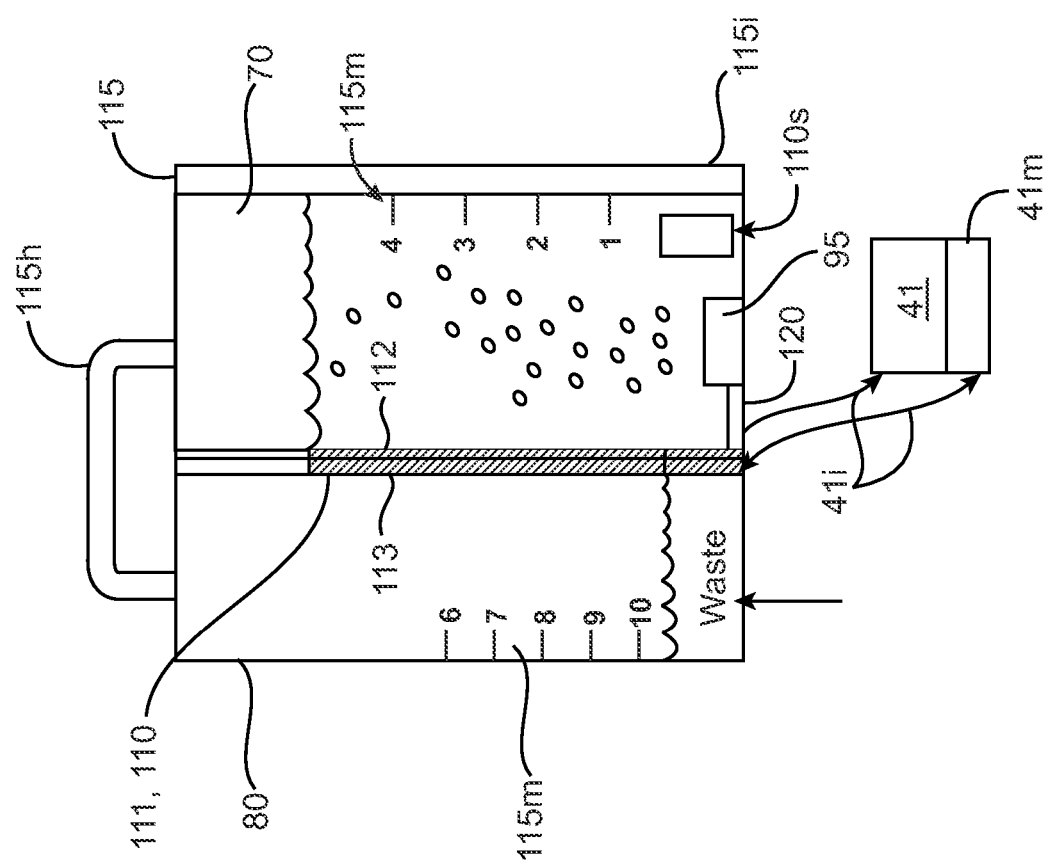
FIG. 2*d* is a lateral view showing a configuration of the fluid reservoir, cooling device and waste container in which the waste fluid is used as a heat sink.
Figure 2E:
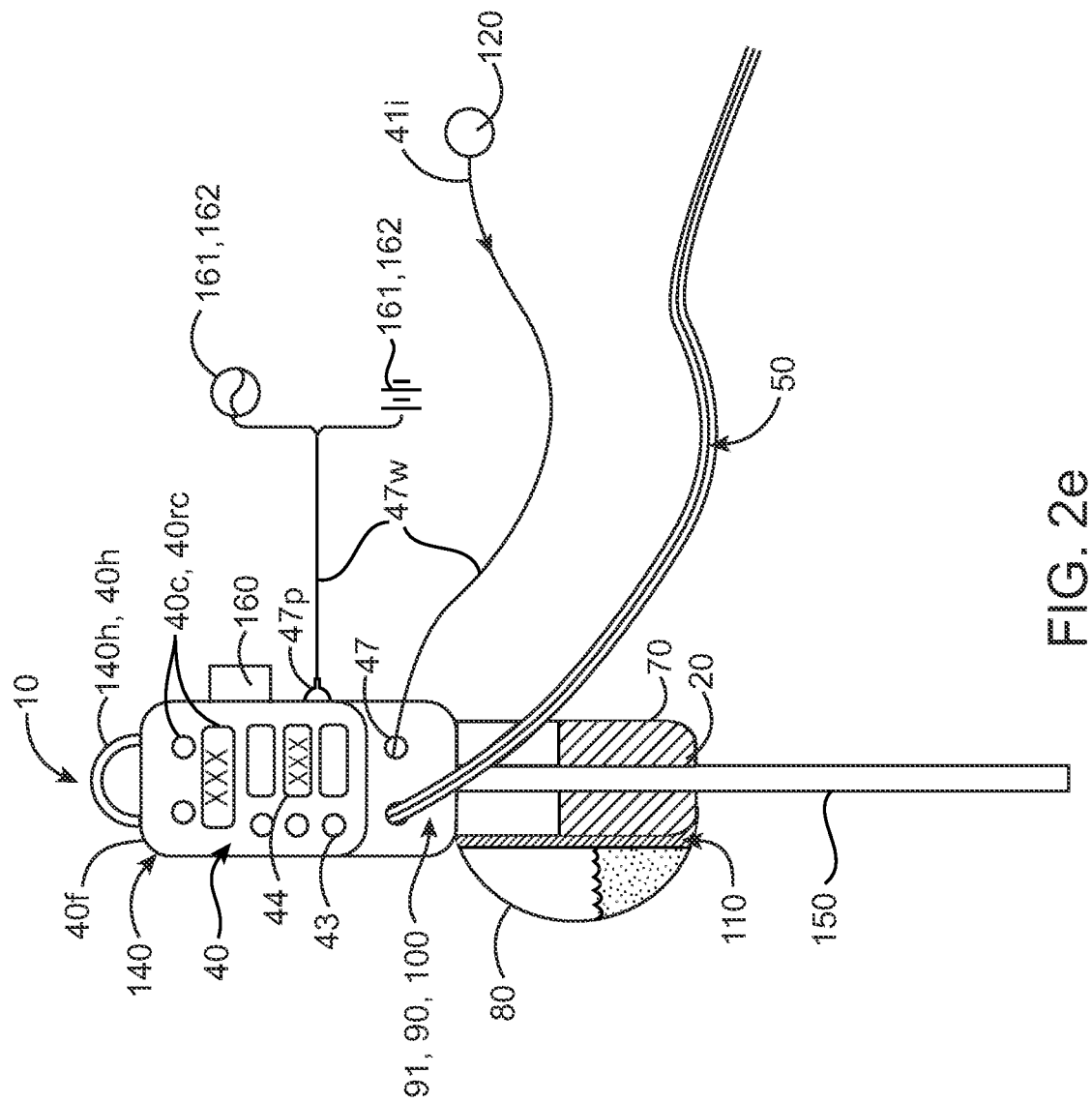
FIG. 2*e* is an elevation view illustrating an embodiment of a portable system unit which includes multiple components of a peritoneal hypothermia system, such as the control unit, fluid reservoir, waste container and a battery.

Cooling device 110 can comprise various cooling devices known in the art including electronic cooling devices, chillers, cryogenic gas based cooling devices and the like. In preferred embodiments, cooling device 110 comprises a peltier cooling device 111 which can be placed within, adjacent to, or is otherwise thermally coupled to reservoir 70 so as to form cooling assembly 115 as is shown in FIG. 2d. Assembly 115 can include volume measurement indicia 115m, one or both of reservoir 70, and container 80 to indicate the fill state of either. It may also include insulation 115i around all or a portion of its surface including the surface of reservoir 70 and container 80. The assembly 115 can include a handle 115h and can be modularized such that it can be reversibly coupled to control unit 40 and/or system unit 140. It can also be configured to be stored in a refrigerator with a filled reservoir 70 such that it can be removed and quickly connected to unit 40/140. In use, such embodiments allow for the immediate infusion of a hypothermic solution 20 without having to wait for a cool down period. Similar results can be achieved by modularizing reservoir 70 such that it can be pre-refrigerated and quickly connected to assembly 115 and/or unit 40/140. Such modularity can be facilitated by the use of quick fluidic connections, such as snap fit connections known in the art, allowing assembly 115 or reservoir 70 to be easily snapped in place.

In preferred embodiments, peltier device 111 is placed between reservoir 70 and waste container 80 such that cooling side 112 of device 111 is thermally coupled to reservoir 70 and the hot side 113 is so coupled to waste container 80. This configuration allows device 111 to readily extract heat from and thus cool the fluid in reservoir 70 and also use the fluid in waste container 80 as a heat sink since that fluid in waste container 80 will still be below the temperature of hot side 113. One or more temperatures sensors 120 can be placed in reservoir 70, container 80, as well as on peltier device 111, so as to send input signals 41$i$ to controller 41. Controller 41 can use these signals to optimize the cooling process using various control algorithms (e.g., PID, PI, etc) embedded within a thermal control module 41$m$. These and related embodiments allow for rapid and continuous cooling of infused fluid 20 with reduced cooling power requirements. In various embodiments, the assembly can also include a supplemental cooling device 110$s$ to provide for faster cooling rates. Supplemental device 110 can be peltier or other cooling devices described herein.

In many embodiments, unit 40 can be integral or otherwise coupled to one or more of reservoir 70, waste container 80, pump or other pressure source 90, and cooling device 110 so as to comprise a system unit 140. System unit 140 is desirably a portable unit and will typically include a handle 140$h$ and is sized to be readily carried and transportable in an ambulance, EMT vehicle, crash cart and the like. Unit 140 can also include brackets or other mounting means to be quickly mounted to an IV pole 150 or like structure. Unit 140 may also include an integral IV pole 150 as is shown in FIG. 2$e$. Pole 150 may be telescoping or otherwise self-expanding. Unit 140 can include an integral battery 160, such as a rechargeable lead acid battery having sufficient capacity for multiple hours of operations. The unit can also include electrical power connections 47$p$ for connection to an external power supply 161 which can be either an AC or DC power supply 162 and 163 respectively.

Pressure source 90 is desirably configured to provide sufficient pressure for fluid flow from reservoir 70 through catheter 50 and into cavity C. In various embodiments, pressure source 90 can comprise an infusion pump including a positive displacement pump or a peristaltic pump. It can also be configured to interface with a pump cassette portion 51 of catheter 50 such that the pump does not need to contact fluid 20. Pump 91 can also be configured as a vacuum source 100 by pumping in an opposite direction. Pump 91 or other pressure source 90 (e.g., a gas source described below), desirably provides sufficient pressure to infuse 2 to 4 liters of solution 20 into the peritoneal cavity of a patient in ten minutes or less. Pump 91 is desirably automated and can send and receive one or more inputs from controller 41. In particular embodiments, pump 91 can be configured to produce pulsatile flow (for either infusion or removal of solution) and can include a selectable pressure and/or flow wave form such as sinusoidal, square wave and like waveforms. The period of the waveform can also be synchronized with one or more of heart rate, respiration as is described herein. In one embodiment, infusate flow can be counter-pulsated (e.g., approximately 180° out of phase) with the heart rate so as to increase blood flow through the peritoneal vasculature and provide a measure of pumping assistance to the heart. In related embodiments, such counter pulsation or other forms of synchronized flow can also be used to increase the patient's blood pressure (by producing vasoconstriction within the peritoneal and surrounding vasculature) for treatment of patients suffering blood loss, shock or other conditions causing low blood pressure. In various embodiments, the waveform and periods of infusion and removal, as well as synchronization, can be controlled by a duty cycle module 41$m$ executed by controller 41. Synchronization can be achieved through inputs of one or more sensors 120, as well as inputs from external biomedical monitoring instrumentation.

In other embodiments, pressure source 90 can comprise a compressed gas source 92, such as a compressed air source. The compressed gas source will typically include a control valve 94 which can be an electronic valve operably coupled to controller 41. Control valve 94 (or other control valve 45) and controller 41 can also be configured to produce the forms of pulsatile and synchronized flow and related waveforms described above for pump 91.

In preferred embodiments, gas source 92 is a compressed oxygen source 93 which can be externally coupled oxygen source or an integral source coupled to unit 40 or 140. Compressed oxygen source 93 is desirably configured to provide sufficient total pressure for fluid flow into cavity C. It's also desirably configured to have a sufficient oxygen partial pressure to oxygenate infused solution 20 so as to be able deliver sufficient oxygen to peritoneal or other tissue to help increase the blood oxygen saturation of a hypoxic patient.

Oxygen source 93 can be coupled to oxygenation element or device 95 such as a bubble oxygenater or hollow fiber oxygenater. Oxygenation device 95 can be positioned within reservoir 70, an oxygenation chamber fluidically coupled to reservoir 70, or within a lumen of infusion catheter 50. The flow of oxygen into solution 20 can be controlled through the use of one or more oxygen sensors 120 positioned within reservoir 70, or infusion catheter 50. Controller 41 can receive one or more feedbacks from these sensors to regulate the oxygen saturation of solution 20 using an oxygen control module 42$m$ which uses one or more control algorithms, e.g., PID, etc. Also, multiple oxygen sensors can be externally placed along the length of infusion catheter 50 in order to measure oxygen partial pressures within different locations within the peritoneal PC or other cavity C as well as a rate of oxygen uptake by peritoneal tissue. Such measured oxygen partial pressure can be utilized together with measured peritoneal pressures and temperatures to more precisely control the infusion and removal of solution from the peritoneal cavity for a hypothermic, resuscitative, dialysis or other medical treatment using an infused solution.

Referring now to FIGS. 6$a$-6$e$ and FIGS. 7$a$-7$e$, several alternative embodiments for preventing peritoneal injury during advancement of infusion catheter 50, will now be discussed. In these embodiments, the catheter can include an unsupported tissue penetrating tip 57$tp$, which can comprise a needle or other sharp tip. They can also be utilized with embodiments where the catheter is advanced through use of advancement member 30 and is tissue penetrating when supported by the advancement member. In an embodiment shown in FIGS. 6$a$-6$e$, catheter 50 can include a slidable protective sheath 50$s$ which allows the tissue penetrating tip 57$tp$ of the catheter to penetrate the skin S and subcutaneous tissues layers STL but will not penetrate the bowel B. Once exposed to the tension of the skin and subcutaneous tissues, the sheath 50$s$ is retracted proximally exposing tip 57$tp$ so that it can pierce the underlying skin and other tissue. Once this tension is relieved though, the sheath springs back over the tip, thereby protecting the bowel. A temperature sensor 120 can be positioned near the tip to detect movement of the sheath (by detecting a change in temperature when this occurs), as well as measure temperature in the peritoneal or other cavity.

In another embodiment shown in FIGS. 7a-7e, pressurized air flow through the catheter 50 can be employed to prevent organ injury during advancement. The air or other fluid 20 is channeled through a lumen 52 to the tissue penetrating tip 57tp of catheter 50. Once inserted subcutaneously (See FIG. 7c) the air or fluid is urged forward, but is incapable of flowing due to the resistance from encroaching subcutaneous tissue ST. Once the needle enters the peritoneal cavity PC though, the bowel B will be moved away from the tip 57tp, creating a gap G, due to the pressurized air fluid forcing it away as is shown in FIGS. 7d and 7e. Desirably, gap G is of sufficient distance such the tip 57tp will not contact the bowel or other peritoneal tissue during movement or repositioning of the catheter. The Gap can be monitored under image guidance or through a sensor 120 and the pressure of fluid 22 can be adjusted to maintain or change the gap distance at the user's preference.

In various embodiments of methods of using the invention, system 10 can be used to cool the patient's body temperature at different rates and different temperatures. Generally, though not necessarily, the patient's body temperature that is cooled is considered to be their core temperature. However, in some instances, system 10 can be configured to produce a more localized cooling effect or otherwise preferentially cool a particular targeted region of the body to a particular temperature (e.g., the peritoneal region), or even a particular organ (e.g., the heart), or an extremity (e.g., the leg) without necessarily bringing the patients core temperature to that level. This can be facilitated by placement of one or more sensors 120 at the target tissue site to be cooled (e.g., in the peritoneal cavity, or a needle sensor inserted into the extremity).

System 10 can be used to produce a particular hypothermic or cooling regimen (e.g. rate of cooling and target temperature). The cooling regimen can be titrated to treat a variety of medical conditions including stroke, myocardial infarction, blood loss or any condition causing reduced perfusion to the brain, heart or any of the major organ systems, e.g. the kidneys, gastro-intestinal, system, etc., as well as any extremity, e.g. arm, leg, etc. In particular embodiments, the cooling regimens can be employed to treat particular conditions e.g., stroke vs. myocardial infarction so as to reduce the amount of ischemic reperfusion injury to vital organs resulting from the particular ischemic event. In specific embodiments, the cooling regimen can be configured to do one or more of the following: i) reduce coronary infarct size and related sequelia from various cardiac events such as acute myocardial infarction, cardiac arrest, arrhythmia, trauma or other cardiac insufficiency; ii) reduce cerebral infarct size and related sequelia from stroke, cerebral vessel dissection, head trauma, cardiac arrest, arrhythmia, blood loss or other cardio-pulmonary insufficiency; iii) reduce tissue injury in other vital organs from cardiac arrest, blood loss or other cardio-pulmonary insufficiency; iv) reduce tissue injury in an extremity (e.g., the leg) resulting from trauma or blood loss; v) reduce post surgical tissue inflammation; and vi) provide a tissue protective effect from reduced perfusion resulting from surgery or other medical procedure.

In various embodiments, the cooling regimen can be selected by the user from a databases of cooling regimens 42db stored memory resources 42 or an external device or computer wireless interfaced to system 10. The database of cooling regimens can include regimens for particular conditions, e.g., myocardial infarction as described above. The user can select a regimen from the database and use it unmodified or may customize, or otherwise fine-tune it to the particular patient and his/her current condition. This can be done by adjusting one more treatment parameters such as infusion rate, infusate temperature, etc.

System 10 can be configured to cool the temperature to a variety of ranges. In many embodiments, the system can be used to cool the patient's temperature in the range of about 30 to about 35° C., with a preferred target temperature of 34° C. Lower ranges can also be selected depending upon the medical condition or surgical procedure. In embodiments for treatment of acute myocardial infarction or stroke, system 10 can be configured to cool the patient's temperature the targeted value (e.g. 34° C.) in ten minutes or less. In many embodiments, this can be achieved by rapidly infusing a bolus of chilled solution into the peritoneal cavity preferably between 2 to 4 liters and more preferably about 3 liters in ten minutes or less. Shorter periods such as five minutes or less are also contemplated and can be achieved through use cooler infusion solutions including solutions cooled below 0° C. Faster cooling can be achieved by infusing cooler solution and/or high infusion rates. Higher flow rates can be achieved through the use of higher pressure or larger lumen diameters for the infusion catheter 50. In particular embodiments, the lumen diameter of the infusion catheter can be configured for delivering a maximum flow rate and the medical care provider can select the infusion catheter for its maximum flow rate so as to able deliver a desired amount of hypothermic solution 20 for a particular medical condition.

Also in various embodiments, system 10 can be used to cool all or a selected portion of the patient's body prior and post surgery to reduce a patient's inflammatory response resulting from the surgery due to the release of cytokines etc. In related embodiments, system 10 can be used for pre-operative and intra-operative cooling of a selected operative site, such as the heart, to allow for extended periods of operation on the organ with reduced or no perfusion through the organ. In one embodiment, the system can be configured to chill the heart (similar to cardioplegia) to allow for various forms of cardiac surgery, which may require the heart to be stopped or where portions of the heart are cross clamped, such as valve replacement, CABG, aorta repair, atrial-septal defect repair and like procedures. This can be achieved through cooling of the peritoneal cavity, or by direct infusion of cooling solution to a chamber of the heart using a cardiac type port access device 60 known in the art.

In such embodiments, system 10 can be configured to achieve coronary tissue temperatures in the range of about 20 to 25° C. or an even lower range for example 10 to 20° C. Lower temperatures can be selected and titrated for longer periods of cardiac arrest or reduced coronary perfusion. For example, for periods of cross clamping less than 60 minutes, a 20 to 25° C. range can be selected, while for periods in excess of 60 minutes a 10 to 20° C. range can be selected. Also, the system can be used to a provide a pre-operative period of hypothermic treatment, also known as pre-ischemic conditioning, to extend operating time and reduce an amount of post operative cardiac reperfusion injury.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the apparatus and related methods can be configured for performing hypothermic treatments at a number of access points in the body including the abdominal, thoracic, spinal and cerebral regions. Embodiments of the apparatus can also be sized or otherwise adapted for pediatric and neonatal applications.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as stand alone elements. Hence, the scope of the present invention is not limited to the specifics of the described embodiments, but is instead limited solely by the appended claims.

What is claimed is:

1. A method of inducing hypothermia in a patient, the method comprising:
    inserting an access device a controlled depth into an abdominal wall of the patient;
    determining entry point into the peritoneal cavity utilizing a sensor output;
    advancing an infusion member through the access device and into the peritoneal cavity of the patient without injuring an organ in the peritoneal cavity;
    monitoring a temperature of the patient at a selected location;
    infusing a hypothermic infusate solution into the peritoneal cavity through the access device or an infusion member positioned within the access device, wherein an infusion parameter is controlled utilizing the monitored temperature;
    cooling tissue in the peritoneal cavity with the hypothermic solution; and
    reducing the temperature of the patient to a selected temperature.

2. The method of claim 1, wherein at least one of a rate of infusion or cooling is titrated to reduce an amount of coronary ischemic tissue injury resulting from myocardial infarction, cardiac arrest or other coronary ischemic event.

3. The method of claim 1, wherein at least one of a rate of infusion or cooling is titrated to reduce an amount of cerebral ischemic tissue injury resulting from stroke, cardiac arrest or other cerebral ischemic event.

4. The method of claim 1, wherein at least one of a rate of infusion or cooling is titrated to reduce an amount of ischemic tissue injury in a tissue extremity.

5. The method of claim 1, wherein at least one of a rate of infusion or cooling is titrated to reduce an inflammatory response resulting from a surgical procedure.

6. The method of claim 5, wherein the surgical procedure is a cardiovascular procedure, an open heart procedure, a valve repair or replacement procedure, an aneurysm repair procedure, a cerebral surgical procedure, a renal procedure or a hepatic surgical procedure.

7. The method of claim 1, further comprising:
    inflating a peritoneal cavity so as to expand an exposed surface area of a peritoneal cavity organ; and
    flowing the hypothermic fluid over the exposed surface area of the peritoneal cavity organ so as to exchange heat or gas with a peritoneal cavity organ.

8. The method of claim 1, wherein the infusion member is advanced using an advancement member positioned within the infusion member.

9. The method of claim 8, further comprising: removing the advancement member once the infusion member has been positioned in the peritoneal cavity.

10. The method of claim 1, wherein a temperature of the solution is in the range of 10 to 20° C.

11. The method of claim 1, wherein the selected temperature is in the range of about 20 to 35° C.

12. The method of claim 1, wherein the infusion comprises infusing a bolus of solution.

13. The method of claim 12, wherein a volume of the bolus is in the range of about 0.5 to 3 liters.

14. The method of claim 12, wherein the infusion further comprises infusing fluid at a controlled rate after completion of the bolus infusion.

15. The method of claim 14, wherein the controlled rate is controlled to maintain the core temperature of the patient at a hypothermic level.

16. The method of claim 1, wherein at least one of the rate or volume of infusate is configured to increase a mean patient blood pressure.

17. The method of claim 1, wherein the infusion parameter is at least one of a flow rate, a pressure, a total infused volume, an inflow duty cycle or a hypothermic solution temperature.

18. The method of claim 1, wherein the selected location is at least one of a tympanic membrane, an intravenous site, an epidermal site, a subcutaneous site or an oral site.

19. The method of claim 1, wherein the selected location includes a plurality of locations and the monitored temperature comprises a composite temperature from the plurality of locations.

20. The method of claim 1, wherein the infusate is infused using a driving force from at least one of a compressed gas source, a gravitational head pressure or a pump.

21. The method of claim 20, wherein the compressed gas source is an oxygen source which is configured to oxygenate the infusate solution.

22. The method of claim 1, wherein the entry point is determined by monitoring a flow rate of infusate solution into the peritoneal cavity.

23. The method of claim 1, further comprising: signaling an entry point event to a medical practitioner performing the method.

24. The method of claim 1, wherein the depth of insertion of the access device into the peritoneal cavity is controlled.

25. The method of claim 24, wherein the insertion depth is controlled through use of a stop positioned on the access device.

26. The method of claim 1, further comprising:
    monitoring a pressure within the peritoneal cavity or the infusion member; and
    titrating the infusate flow rate responsive to the monitored pressure.

27. The method of claim 26, wherein the monitored pressure is utilized to prevent over-filling of the peritoneal cavity.

28. The method of claim 26, wherein the infusate flow rate is titrated responsive to the monitored pressure exceeding a threshold or a rate of increase.

29. The method of claim 1, wherein the access device has a tissue penetrating configuration and a non-tissue penetrating safety configuration.

30. The method of claim 29, wherein the access device assumes the safety configuration after insertion through the abdominal wall.

31. The method of claim 29, wherein the access device includes a slidable sheath that slides over a tissue penetrating portion of the introducer to achieve the safety configuration.

32. The method of claim 29, wherein the access device includes a shearable tissue penetrating portion which when sheared assumes the safety configuration.

33. The method of claim 29, wherein the safety configuration is achieved by pressurizing the access device.

34. The method of claim 27, further comprising:
inserting the access device through tissue in the tissue penetrating configuration; and
converting to the safety configuration when a distal portion of the access device penetrates the distal side of the abdominal wall.

35. The method of claim 1, further comprising: withdrawing at least a portion of the infusate from the peritoneal cavity.

36. The method of claim 35, further comprising: utilizing the withdrawn solution as a heat sink for cooling the infusate solution infused into the peritoneal cavity.

37. The method of claim 36, wherein cooling is performed using a peltier effect device.

38. The method of claim 35, wherein the infusate is withdrawn using a vacuum pressure.

39. The method of claim 35, wherein the infusate is withdrawn at the same access point in the abdominal wall used for infusion.

40. The method of claim 35, wherein the infusate is withdrawn responsive to at least one of an infusion inflow rate, a peritoneal pressure, or a peritoneal temperature.

41. The method of claim 35, wherein at least one of the infusion or withdrawal of the infusate is pulsated.

42. The method of claim 41, wherein the pulsation is synchronized to a heart rate or a respiration rate.

43. The method of claim 35, wherein the infusion and the withdrawal of the infusate are performed in substantially sequential periods.

44. The method of claim 35, wherein the duration and waveform of the infusion withdrawal are configured to optimize at least one of heat transfer with the peritoneal organs, rate of body cooling to a selected core temperature, maintenance of body core temperature at the selected temperature and oxygenation of the peritoneal organs.

45. The method of claim 41, wherein there is an interval between each period of infusion and withdrawal.

46. The method of claim 1, further comprising: oxygenating the infusate solution before infusion into the patient.

47. The method of claim 46, further comprising:
utilizing the infusate solution to diffuse sufficient oxygen through the peritoneal tissue to at least partially meet the oxygen requirements of the patient.

48. The method of claim 46, wherein the infusate solution comprises a fluorocarbon.

* * * * *